(12) United States Patent
Hughes et al.

(10) Patent No.: US 7,913,686 B2
(45) Date of Patent: *Mar. 29, 2011

(54) SELF CONTAINED AEROSOL DUAL DELIVERY SYSTEM (SCADDS)

(75) Inventors: Robert J. Hughes, Lynn Haven, FL (US); Philip J. Paustian, Panama City, FL (US)

(73) Assignee: Scadds Incorporated, Panama City, FL (US)

( * ) Notice: Subject to any disclaimer, the term of this patent is extended or adjusted under 35 U.S.C. 154(b) by 1509 days.

This patent is subject to a terminal disclaimer.

(21) Appl. No.: 11/269,246

(22) Filed: Nov. 8, 2005

(65) Prior Publication Data
US 2006/0054165 A1 Mar. 16, 2006

Related U.S. Application Data

(63) Continuation-in-part of application No. 10/442,120, filed on May 21, 2003, now Pat. No. 7,013,888.

(60) Provisional application No. 60/434,417, filed on Dec. 19, 2002.

(51) Int. Cl.
*A61M 11/00* (2006.01)

(52) U.S. Cl. ......... 128/200.14; 128/200.24; 128/203.12; 128/200.12

(58) Field of Classification Search ............. 128/200.11–200.21, 200.24, 200.26, 200.29, 201.22, 201.26, 128/202.15, 203.12, 203.14, 203.15, 203.18, 128/203.21–203.23, 203.28, 205.25, 206.21; 604/94.01; 131/270–273
See application file for complete search history.

(56) References Cited

U.S. PATENT DOCUMENTS

| | | | | |
|---|---|---|---|---|
| 2,470,297 A | * | 5/1949 | Fields | 128/203.15 |
| 3,964,483 A | * | 6/1976 | Mathes | 128/203.15 |
| 4,393,884 A | | 7/1983 | Jacobs | |
| 4,509,515 A | * | 4/1985 | Altounyan et al. | 128/200.23 |
| 4,800,903 A | | 1/1989 | Ray et al. | |
| 5,002,048 A | * | 3/1991 | Makiej, Jr. | 128/200.23 |
| 5,752,510 A | | 5/1998 | Goldstein | |

(Continued)

*Primary Examiner* — Justine Yu
*Assistant Examiner* — Valerie Skorupa
(74) *Attorney, Agent, or Firm* — James Creighton Wray; Meera P. Narasimhan

(57) ABSTRACT

Self Contained Aerosol Dual Delivery System (SCADDS) is a pocket-sized inhaler for delivering inhaled therapeutic or recreational aerosols simultaneously and separately via oral and nasal routes. A handle assembly has a removable mouthpiece, cartridge penetration needles, puncture needle protective cover, a shuttle, a cam, valves and conduits from the penetration needles to the individual nozzles for oral and nasal inhalation. A cartridge contains separate reservoirs of solutions for oral and nasal inhalation. The reservoirs, impermeable bags with fluid and dissolved gas in solution, are punctured when the cartridge is attached to the handle assembly. Inhalation slides the shuttle toward the mouthpiece and opens the valves to release solution. The oral aerosol is inhaled into the lungs while the nasal aerosol provides a pleasant aroma. To enhance oral inhalation solution properties the oral inhalation reservoir may contain finely divided solids in a semi-permeable membranous bag, attached to a second reservoir, or be divided by a filter such that these solids do not occlude nozzles or penetration needles Degassed water may be used to enhance organic compound solubility in solutions. Alternative reservoir bag systems are twin spring driven or gas driven cylinders to provide proper pressure to aerosolize nasal and oral fluids. Hydraulic intensification, piezoelectric pumping devices, and electromechanically driven pressure pumps are alternative pressurization systems.

18 Claims, 24 Drawing Sheets

U.S. PATENT DOCUMENTS

| | | |
|---|---|---|
| 5,904,140 A | 5/1999 | McGoogan |
| 5,906,203 A * | 5/1999 | Klockseth et al. ....... 128/205.24 |
| 5,941,241 A | 8/1999 | Weinstein et al. |
| 5,957,125 A | 9/1999 | Sagstetter et al. |
| 5,988,160 A | 11/1999 | Foley et al. |
| 6,014,972 A * | 1/2000 | Sladek ..................... 128/203.12 |
| 6,102,036 A | 8/2000 | Slutsky et al. |
| 6,223,744 B1 | 5/2001 | Garon |
| 6,422,240 B1 | 7/2002 | Levitsky et al. |
| 6,503,480 B1 | 1/2003 | Edwards et al. |
| 6,698,426 B1 | 3/2004 | Wright |
| 6,810,874 B1 * | 11/2004 | Koskela et al. .......... 128/203.15 |
| 7,013,888 B2 * | 3/2006 | Hughes et al. ........... 128/200.14 |
| 2002/0170928 A1 * | 11/2002 | Grychowski et al. ......... 222/251 |
| 2004/0025874 A1 * | 2/2004 | Seppl ...................... 128/203.15 |

* cited by examiner

Section 4-4

Section 5-5

Section 6-6

Detail 7

Section 9-9

Section 14-14

Detail 18

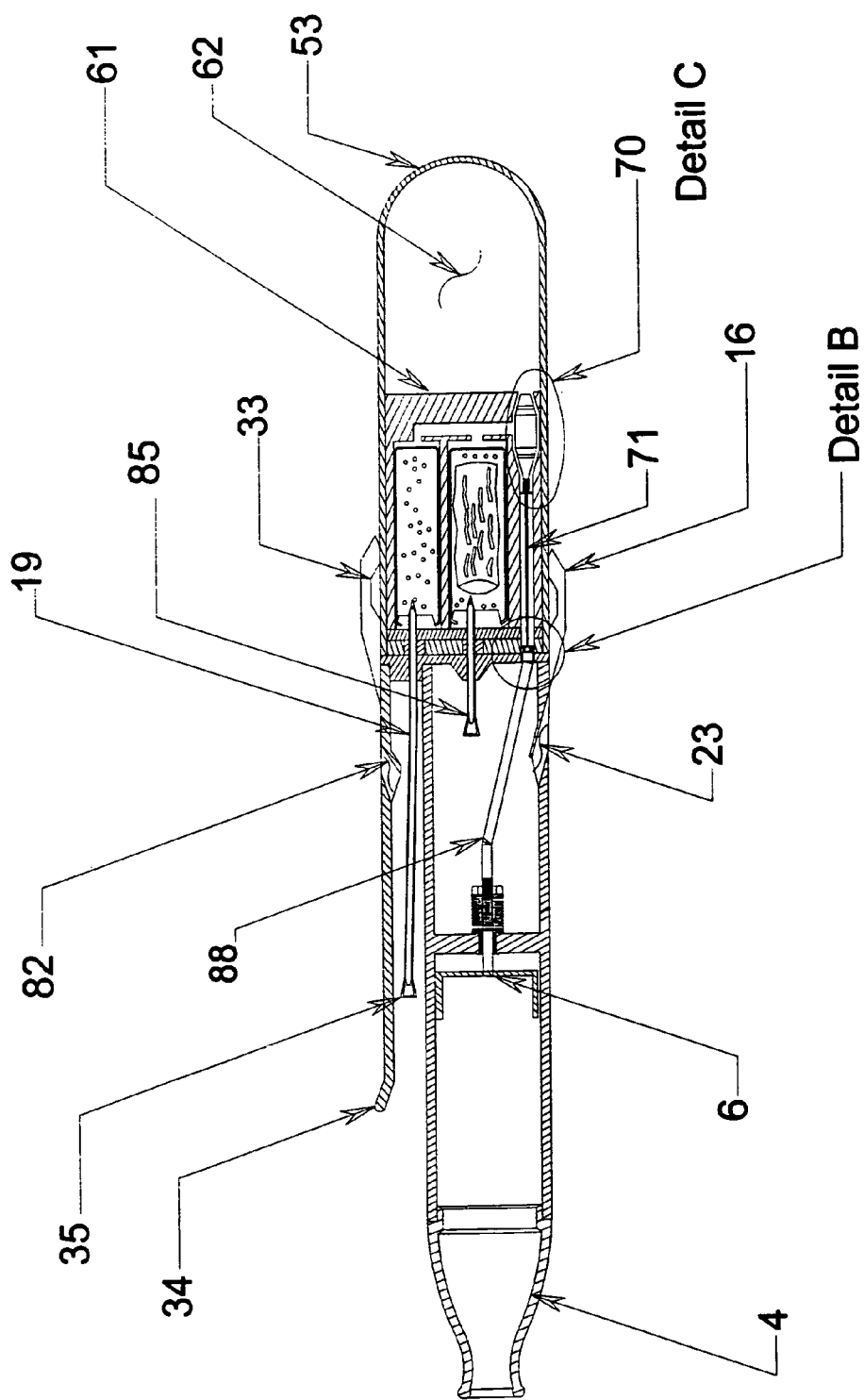

SELF CONTAINED AEROSOL DUAL
DELIVERY SYSTEM (SCADDS)

This application is a continuation-in-part of U.S. application Ser. No. 10/442,120 filed May 21, 2003, now U.S. Pat. No. 7,013,888 which claims the benefit of priority of U.S. Provisional Application No. 60/434,417, filed Dec. 19, 2002, both of which are incorporated herein by reference in their entireties.

BACKGROUND OF THE INVENTION

Inhaled medications need to be delivered more simply and their use made more pleasant than current alternatives permit. Anti-nausea medications need quicker onset of action, a non-oral route, and the option to delay use until symptoms occur rather than forcing the user to be sedated prematurely and possibly needlessly for prophylaxis against the myriad potential causes for nausea: seasickness, motion sickness, or chemotherapy induced nausea.

Similarly the recreational tobacco user who wishes to continue to enjoy tobacco products needs a means to do so without annoying non-tobacco users and ideally a means that provides greater pleasure.

For the asthmatic or other pulmonary disease patient who requires inhaled medication the special coordinated breathing to use a metered dose inhaler is a skill perfected by scarcely half of users. Current devices do not adequately allow for simultaneous delivery of potentially different aerosol solutions to the nose and lungs. Devices currently available do not always adequately diffuse and deposit aerosol solutions in the most peripheral branches of the bronchial tree. Therefore, diseases such as immune mediated diabetes mellitus, depression, Alzheimer's disease, erectile dysfunction, and other ailments cannot be treated properly with aerosolized solutions.

Needs exist for improved portable pocket-sized inhalers for delivering inhaled therapeutic or recreational aerosols simultaneously and separately via oral and nasal routes.

SUMMARY OF THE INVENTION

The present invention is a Self Contained Aerosol Dual Delivery System (SCADDS) that provides simultaneous delivery of potentially different aerosol solutions to the nose and the lungs. Key to the successful performance of this device is its novel methods for creating an aerosol suitable for maximum diffusion and deposition in the most peripheral branches of the bronchial tree. It offers the opportunity to broaden the ailments treated via inhaled medications beyond pulmonary diseases to include ailments ranging from immune mediated diabetes mellitus to depression, Alzheimer's disease, erectile dysfunction, and others depending on what solutions one creates to aerosolize. Degassed water can be used to enhance an organic compound's aqueous solubility and thus broaden the choice of compounds for aerosolization. A biologically tolerable gas such as nitrogen or carbon dioxide may be dissolved under pressure in the solutions created to improve aerosolization in some embodiments.

SCADDS, by mimicking aspects of smoking a cigarette, can deliver medication to the pulmonary disease patient in a manner they will enjoy and be familiar with in many cases from the activities that initially contributed to their illness. Dispensing effort can be reduced for patients with limited inspiratory capacity.

For the tobacco user wishing to have a smokeless tobacco product that provides equal or superior pleasure to traditional means, SCADDS can deliver an aerosol of tobacco extracts mixed in water, salt water, dilute alcohol, or in some combination of these and other solutions to create a solution that is buffered to physiologic pH. Degassed water or degassed salt-water can also be used to enhance organic compound solubilities. This tobacco extract solution bathes finely chopped tobacco leaf fragments and other tobacco plant fragments that are separated by a filter from the rest of the oral inhalation contents bag, encased in a semi permeable membrane bag that permits molecules to freely mix with the larger oral contents bag, or contained in a canister that is attached to the oral contents reservoir bag by a one-way valve or filter that permits continuous enrichment of the solution as soluble and volatile components from the tobacco continue to diffuse into the solution until soluble tobacco components are distributed uniformly throughout all regions or compartments. These approaches or a combination of them prevent clogging the nozzle or one-way valve by stray tobacco solids but facilitate free circulation of the fluid over the tobacco leaf fragments to increase flavor. To help subsequent aerosolization all the solutions may have gas dissolved in them either before mixing with tobacco fragments and extracts or in the case of degassed fluids gases such as nitrogen or carbon dioxide will be added back to the degassed fluids after mixing with the tobacco such that further organic compound extraction has occurred prior to dissolving in gas to aid aerosolization.

A pleasant aroma is supplied via an aerosol from the nasal contents bag simultaneously with inhaling from the oral contents bag to further enhance the user's sensory experience.

The absence of prolonged contact of tobacco products with the same patch of buccal mucosa as well as the absence of combustion products and carbon monoxide makes the SCADDS device preferable for the discerning tobacco consumer who desires maximum immediate satisfaction. In addition, the recreational tobacco consumer avoids all fire hazards associated with tobacco use since SCADDS uses no fire or heater elements that might ignite. Since there is no combustion the SCADDS device produces neither first-hand nor second-hand smoke. The tobacco consumer also avoids the inconvenience of searching for somewhere to spit the product out when they are done with it since they are inhaling it.

For the merchant stocking Cigines, the name for the handle and mouthpiece, and Cleantines, the name for the cartridges, for the tobacco consumer product, the design offers improved shelf life because the tobacco extract solution will improve in quality over time since it is enriched by the diffusion of components from the tobacco plant fragments in the tobacco portion of the Cleantine cartridge.

In its simplest embodiment the Self Contained Dual Aerosol Delivery System consists of a bag or bags of solutions pressurized with dissolved gas to aid in aerosolizing the solution. To keep the gas in the bags in solution and provide sufficient driving pressure they are encased in a cartridge designed to be pressurized to the same pressure as the reservoir bags. The reservoir bags are exceedingly compliant so that almost no energy is lost deforming the elastomeric or polymeric reservoir bags.

A more complex alternative to the reservoir bag system consist of twin spring driven or gas driven cylinders to provide proper pressure to nasal and oral fluids to aerosolize them upon ejection through their respective orifices. This is also necessary to keep dissolved gas in solution that is essential for producing the most efficient aerosolization. Other alternative equivalent schemes for providing the pressure necessary to produce twin aerosols for oral and nasal inhalation of the same or different substances include hydraulic intensification (akin to gas powered fuel injection) to improve aerosolization, piezoelectric pumping devices, electromechanically driven pressure pumps, or the aforementioned spring driven system.

For dose dependent medical or recreational embodiments of the Self Contained Aerosol Dual Delivery System sonic orifices are incorporated such that the flow through each orifice remains constant.

In its most fundamental embodiment a shuttle mechanism that is activated by the pressure across the shuttle created by placing the SCADDS mouthpiece in the mouth and inhaling releases an aerosol that sprays out the main contents valve seat and through the nozzle to form an aerosol of three micron sized particles. The inhaled atmospheric gas starts its journey through vents in the sides of the central tube near the cartridge attachment, triggers the shuttle motion when sufficient flow occurs, and entrains the aerosol spray that the shuttle motion and subsequent valve release permits. The inhaled air stream continues through the shuttle and mouthpiece to draw the aerosol through the oral cavity, trachea, and major bronchi and into the distal airways of the lung to diffuse to the most peripheral alveoli rapidly. The small particle size favors only minimal deposition of the aerosol in the oral cavity, trachea, or large airways, prior to reaching the alveoli. Concurrently a cam activated second nozzle sprays an aerosol in the direction of the nose. The breath stream inhaled through the nasal content entrainment passage entrains the nasal aerosol flow and carries it into the nasal passages to trigger pleasant olfactory sensations.

The dissolved gas in both solutions is critical to facilitating the best aerosolization possible. This is because in addition to the aerosolization caused by the passage of the liquid through a designed orifice under pressure the dissolved gas coming out of solution as pressure drops creates myriads of micro bubbles imparting additional large quantities of random kinetic motion resulting in smaller mean particle size in the aerosol stream. The gases used will be soluble in the solutions but inert to the chemical constituents and safe for human and environmental health. Nitrogen and Carbon Dioxide are among the suitable gases.

In order for the nasal inhalation process to occur synchronously with the aerosol inhaled through the mouthpiece a cam on top of the shuttle allows the dispensing valve for the nasal solution to be opened as it rides onto a lower portion of the cam profile. This unique feature allows the nasal mechanism to be stopped and started independently of the shuttle motion. By substituting new cam profiles the opening and closing of the nasal aerosol valve can be adjusted to an infinite set of dispensing times.

Both can be fed from a common reservoir bag or more often separate bags that will allow the aroma aerosol to have no relationship to the aerosol delivered to the lungs. The merit of this approach is that it allows the user who is not focused on breathing just through his mouth or his nose but instead doing both to inhale two different substances at one time if that is desired. For example an insulin solution could deliver human DNA derived insulin to the lungs in small doses while the user was eating and taking puffs on the SCADDS device between bites. The insulin solution would be inhaled and entrained to the lungs while the nasal aroma solution might as an example provide a cinnamon or Vanilla aroma to enhance the pleasure the diabetic user took from his meal.

The reservoir bags are encased in a cartridge that inserts into the mouthpiece handle assembly end distal to the detachable mouthpiece. The entire product should fit conveniently in pocket or purse in the embodiments suitable for insulin, asthma medications, or tobacco extract delivery. The space in the cartridge outside the reservoir bags is filled with pressurized gas so that the bags inside the cartridge are not exposed to a significant pressure gradient since they will be filled within the cartridge and synchronously with pressuring the space outside the reservoir bags. This approach will allow the bags to be made from very thin, inexpensive, flexible polymer or elastomeric materials. The bags have integral self-sealing tops that allow filling during production and immediate resealing when the filling needles are removed.

For delivering a tobacco extract the design is augmented with a filter dividing the oral contents inhalation solution bag into a region with tobacco leaf fragments and a region without tobacco leaf fragments but in continuity at a molecular level, or a tobacco canister within the cartridge and connected to the oral contents reservoir by a filter or one-way valve. Alternatively, a semi-permeable membranous bag containing the tobacco fragments within the oral inhalation solution allows molecular diffusion while eliminating requirement for the dividing filter, one-way valve, and tobacco canister. In tobacco containing embodiments the cartridges are called Cleantines while the mouthpiece and handle assembly is called a Cigine. A Cigine will be used repeatedly as the user inhales aerosols from successive Cleantines. The one-way valve connects the tobacco leaf canister to the oral inhalation contents reservoir bag permitting free diffusion of components down their concentration gradients when the user is not actively inhaling. The semi-permeable membranous bag and the filter embodiments both allow diffusion at all times.

For delivering Albuterol or other solution for asthma or rapid acting inhaled insulin solution for diabetes or other therapeutic uses the device will simply be referred to as a SCADDS.

For delivering albuterol, ipratroprium bromide, pirbuterol acetate or other bronchodilator medication aerosols to the lungs in an incremental breath-driven manner the device functions such that each successive dose allows recruitment of more small airways thanks to the action of the prior dose. Patient compliance is aided by a release of a pleasant aroma inhaled nasally while the medication is inhaled orally. In the event the patient doesn't require the extra reinforcement of the aroma cartridge that portion of the device can be rendered inactive. The lack of any requirement for training to use the device since the activity will be similar to smoking is an additional advantage that the pulmonary disease medication application offers. The medication doses are contained in individual cartridges that the user will inhale typically over six to nine minutes during multiple breaths.

For delivering insulin solutions the device provides three micron sized particles in an aerosol inhaled intermittently during a meal. Aerosolization of insulin solutions thus changes any injectable regular insulin into predictable rapid acting inhaled insulin because absorption through the alveoli is much faster than subcutaneous absorption after injection. Thus an insulin solution could deliver human DNA derived insulin to the lungs in small doses while the user was eating and taking puffs on the SCADDS device between bites. The insulin solution would be inhaled and entrained to the lungs while the nasal aroma solution might provide a cinnamon or vanilla aroma to enhance the pleasure the diabetic user took from his meal. Cartridges of insulin solution and aroma solution would typically hold ten to twenty units of insulin and be stable for twenty-four hours after puncture. Thus a user might inhale 6 breaths of insulin during a meal that would require six units and 10 breaths for 10 units for a larger meal and the type II diabetic eating more and with more insulin resistance might require the 20 unit cartridge and take twenty breaths from his insulin cartridge during his potentially larger meal or to cope with his insulin resistance.

A system called the Cigine that combined with cartridges called Cleantines provides a version of the Self Contained Aerosol Dual Delivery System to deliver an aerosolized tobacco extract for the recreational tobacco user via the oral inhalation route while simultaneously delivering an aroma from a separate aroma reservoir that is inhaled nasally. The aroma substance can also be a solution of a tobacco extract or be independent to mimic use in other parts of the world where tobacco may be flavored with cinnamon, cardamom, or other compounds. In different embodiments aroma may be dispensed by driving either compressed gas or air over a liquid or solid or blowing it through a liquid confined by surface tension or capillary action when not receiving pressure thus eliminating the need for a nasal contents bag. In some cartridges for the recreational tobacco user most intent on mimicking prior tobacco use experiences, a small amount of cured tobacco will be sprayed with compressed gas to blow the volatile aroma compounds directly to the nostrils eliminating aerosol generation from solution for the nasal pathway.

In general the decoupling of tobacco extract and aroma should create a superior sensory experience for the recreational tobacco user along with the benefits of little to no tar, no carbon monoxide, no second-hand smoke production, and no need to be spitting the product out after use as in some smokeless tobacco products. Thus this system lets the recreational tobacco user enjoy tobacco without annoying, inconveniencing, or possibly endangering their neighbor any more than an office mate in the next cubicle having a cup of hot coffee and a doughnut. To further enhance the no neighbor annoyance feature a version of the Cleantine cartridge will be offered that eliminates the nasal solution or olfactory sensation source. This Cleantine cartridge will consist of the usual solution of water, salts, refined tobacco extracts, dissolved gas to aid aerosolization and possibly a small amount of alcohol to enhance organic compound solubilities in the solution that fills the oral inhalation reservoir and the tobacco canister. This oral inhalation solution bathes the tobacco leaf and other tobacco plant fragments in the tobacco cartridge that continue to give off compounds to enrich the solution as a whole until it is inhaled as an aerosol in the manner outlined previously in the summary of the invention and subsequently in the description of the drawings.

The recreational tobacco user will determine which cartridge is preferred for his or her pleasure over time. Special versions for use in low pressure (for example climbing Mount Hood or driving up Pikes Peak), high pressure, low ambient temperature (for example winter in Boston, Mass.), high ambient temperature (for example Death Valley, Calif.) can be manufactured for specialized markets by modifying the Cigine by altering the shuttle, including the adjustment screw, or producing Cleantine cartridges with different pressures.

The device functions for delivering an aerosolized solution of water soluble vitamins such as B12, folate, thiamine, etc. along with a pleasant aroma solution. This mode of taking vitamins may offer the user more pleasant alternative to the widening list of pills he or she swallows each morning to supplement their diet and puts the vitamins into the blood stream faster than oral routes permit.

The device functions as a system for delivering inhaled medication for relief of nausea from seasickness, airsickness, chemotherapy, or other causes. The SCADDS system is readily adaptable to treating nausea by creating an oral inhalation solution aerosol with scopolamine, tetrahydrocannabinol, meclizine, or other anti-nausea medications that the user inhales with the same ease he might smoke a cigarette on a pitching and rolling deck. For seasickness and chemotherapy nausea, the nasal aerosol pathway would be inactive in most embodiments since almost any smell is unsettling to the truly nauseated. The rapidity of onset allows the user to avoid being overly sedated by taking prophylactic anti-nausea remedies prior to onset of symptoms.

The device functions as a system for delivering inhaled acetylcholinesterase inhibitors and butylcholinesterase inhibitors for the treatment of Alzheimer's disease and multi-infarct dementia. The ease of use of the SCADDS system with the reinforcement provided by a pleasant aroma accompanying each dose of medication should appeal to the Alzheimer's patient and their caregiver. Reducing the stimulus to excess stomach acid production since the inhaled route will reduce dosage requirements is another advantage.

For therapeutic applications the cartridges can be supplied with an exact dose such that the entire dose is completely delivered upon exhaustion of the cartridge. The user will be aware of this by the synchronous decline is olfactory sensation.

A system in which the SCADDS mouthpiece, handle assembly, and cartridge are combined as a single disposable unit for one time medical or recreational use can be produced.

In an alternative embodiment of the Self Contained Dual Aerosol Delivery System the mouthpiece and handle assembly are free of valves and devoid of cam-lock assembly. It still contains a shuttle on a shaft and penetration needles. When the mouth-piece handle assembly is connected to the cartridge, the shuttle shaft hooks to a valve in the cartridge. Inhaling moves the shuttle which opens the valve which permits gas from the pressurized gas reservoir in the cartridge to provide external driving pressure on the oral solution and nasal solution inhalation bags such that their contents release through the penetration needles that connect to nozzles in the mouthpiece handle assembly as before.

The cartridge valve system is normally biased closed via gas pressure or spring force such that once inhalation pressure drops below valve opening pressure the gas flow stops and delivery of oral and nasal aerosols ceases. The cracking pressure of the valve can be controlled by adjusting spring pressure again for different applications as before. In this configuration the cartridge valve only needs to function reliably for delivery of a single cartridge's contents. This may allow less expensive valve components and eliminates concerns about cleaning the mouthpiece handle assembly between uses to preserve reliable function. The reservoir bags are exceedingly compliant. Therefore almost no energy is lost deforming the elastomeric or polymeric reservoir bags.

These and further and other objects and features of the invention are apparent in the disclosure, which includes the above and ongoing written specification, with the drawings and the claims.

DETAILED DESCRIPTION OF THE DRAWINGS

Figure 1:
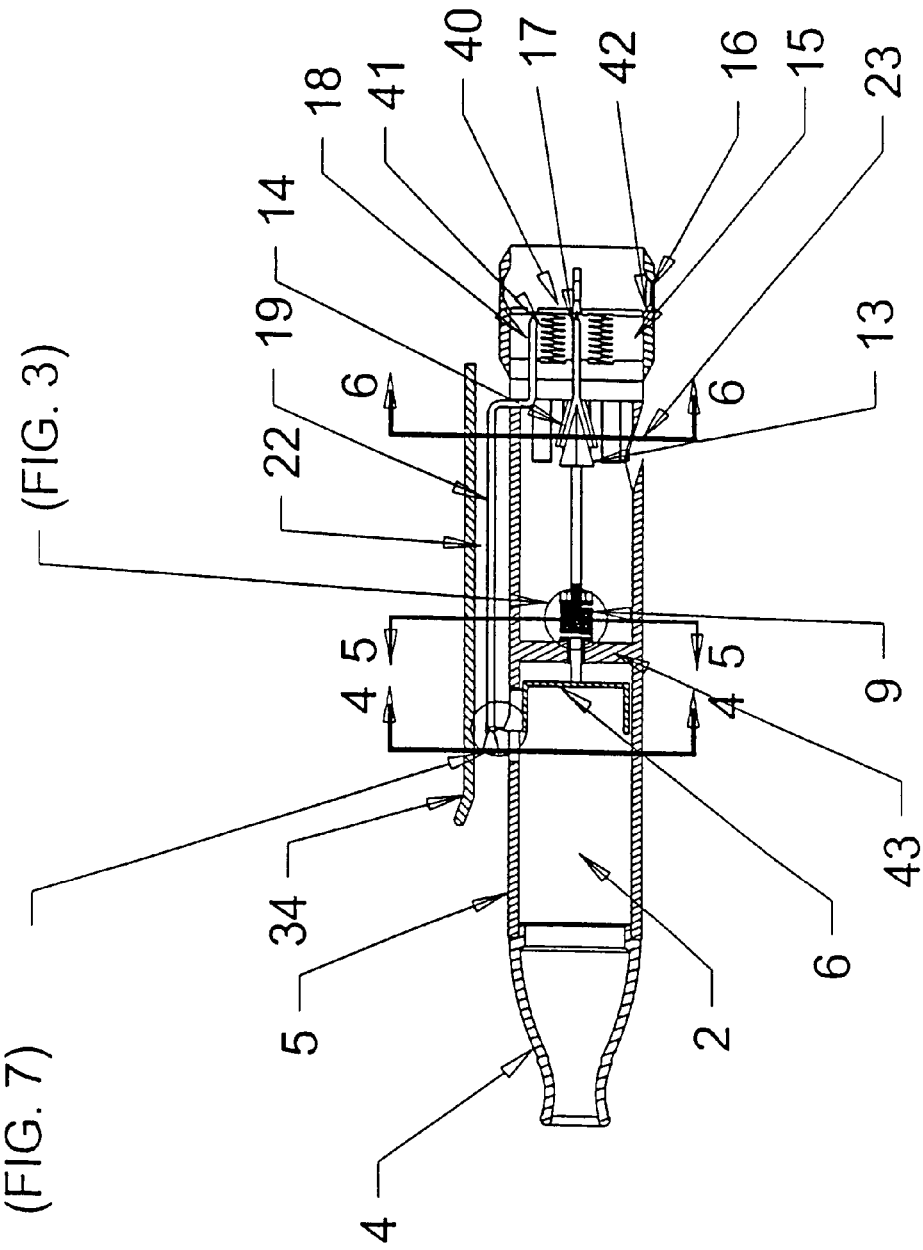
FIG. 1 is a cross-sectional side elevation drawing of a generic SCADDS with cartridge removed showing how the puncture needle protective plate extends.
Figure 2:
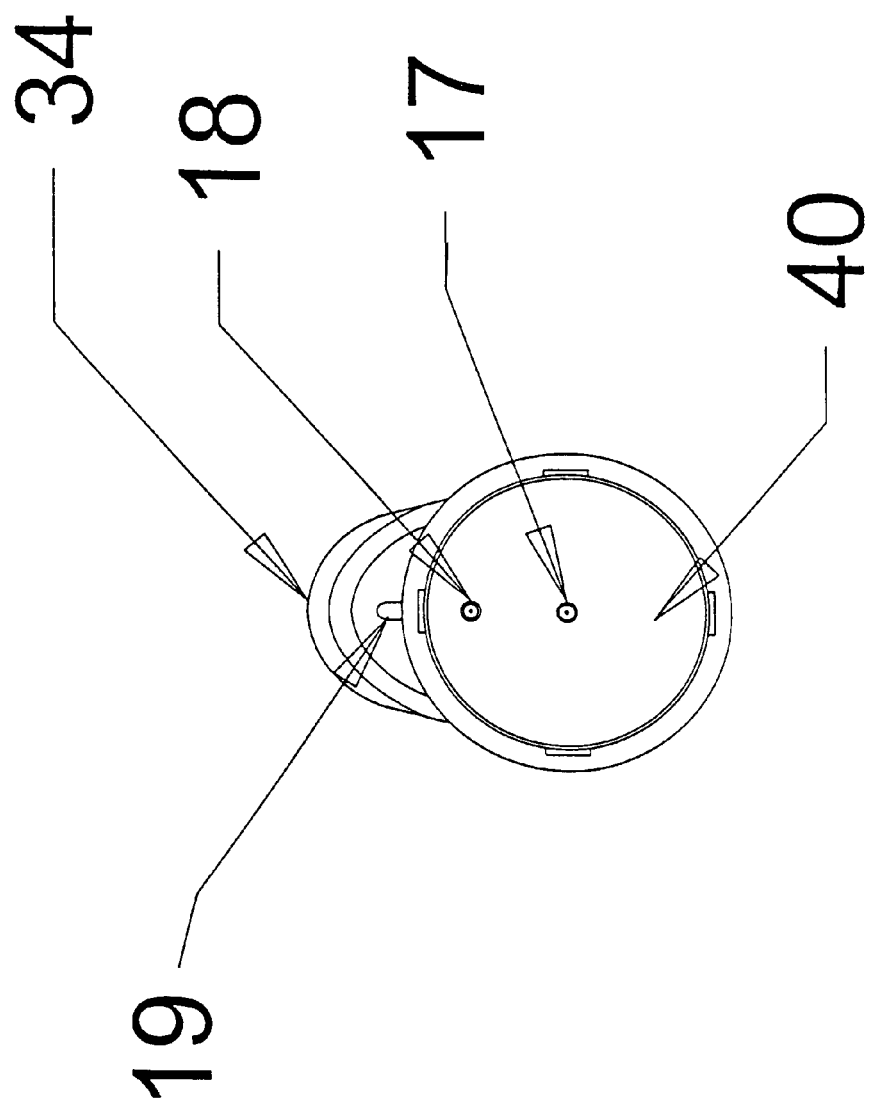
FIG. 2 is a front elevation view of the device with front defined as the cartridge-accepting end of the device.
Figure 11:
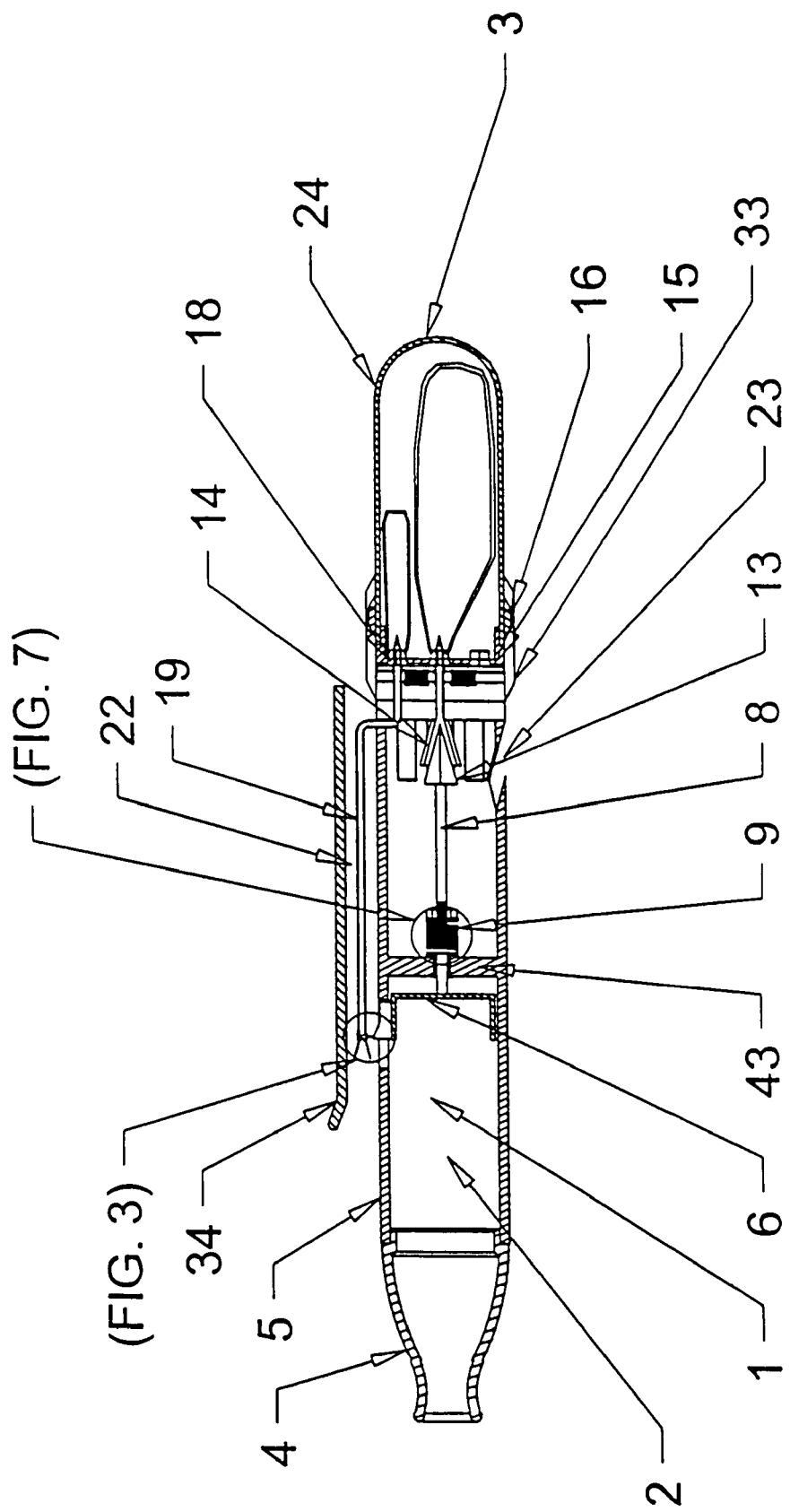
FIG. 11 is a cross sectional side elevation view of a loaded SCADDS shown in FIG. 1 with the cartridge shown in FIG. 8, FIG. 9, and FIG. 10, attached to it.

Referring to FIG. 1, FIG. 2, and FIG. 11, to activate the device 1 in FIG. 11 the user simply holds the handle assembly 5, places the mouthpiece 4 in his lips, and inhales, making no special effort to breathe just through his mouth. The low-pressure zone generated by the flow of gas through the decreased open area in the main shuttle 6 moves the shuttle 6 towards the user's mouth. The shuttle openings are designed to aid in aerosol mixing with the inlet air stream and to maximize flow efficiency. As illustrated in FIG. 1 the main shuttle 6 is connected to the shuttle valve-connecting shaft 8 and then to the main contents shutoff valve 13, which before inspiration is held tightly against the main contents valve seat and nozzle 14.

Figure 3:
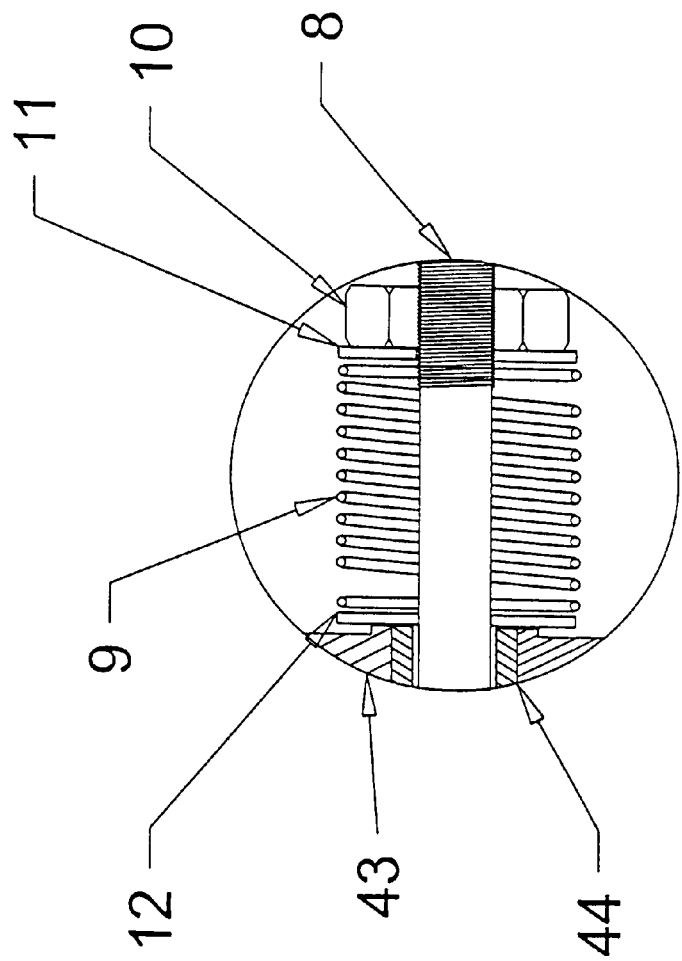
FIG. 3 is a detail from FIG. 1.

As shown in FIG. 3, a detail from FIG. 1, the valve seat and nozzle 14 shown in FIG. 1 is held shut by the shuttle cracking pressure of spring 9, which is held between the forward spring retaining washer 11 and the aft spring retaining washer 12 which are further held in place against spring force by the shuttle cracking pressure adjustment nut 10.

Figure 5:
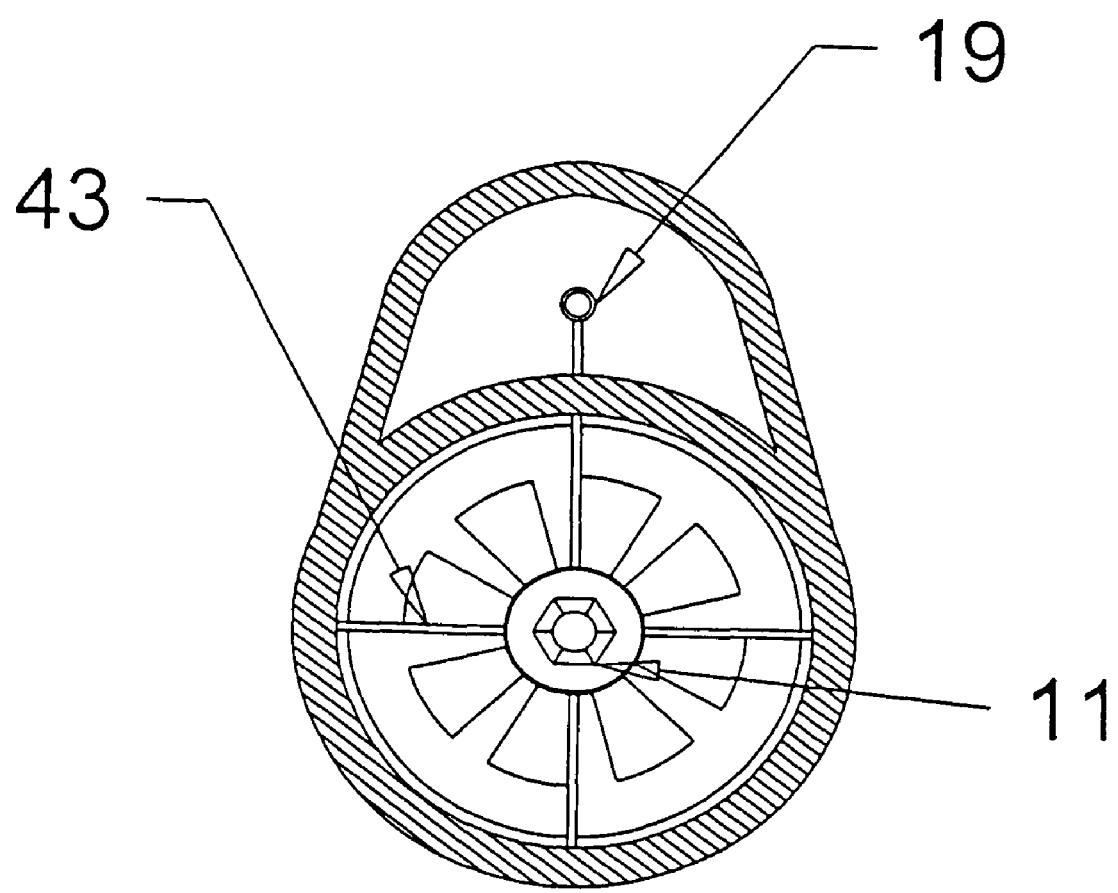
Figure 6:
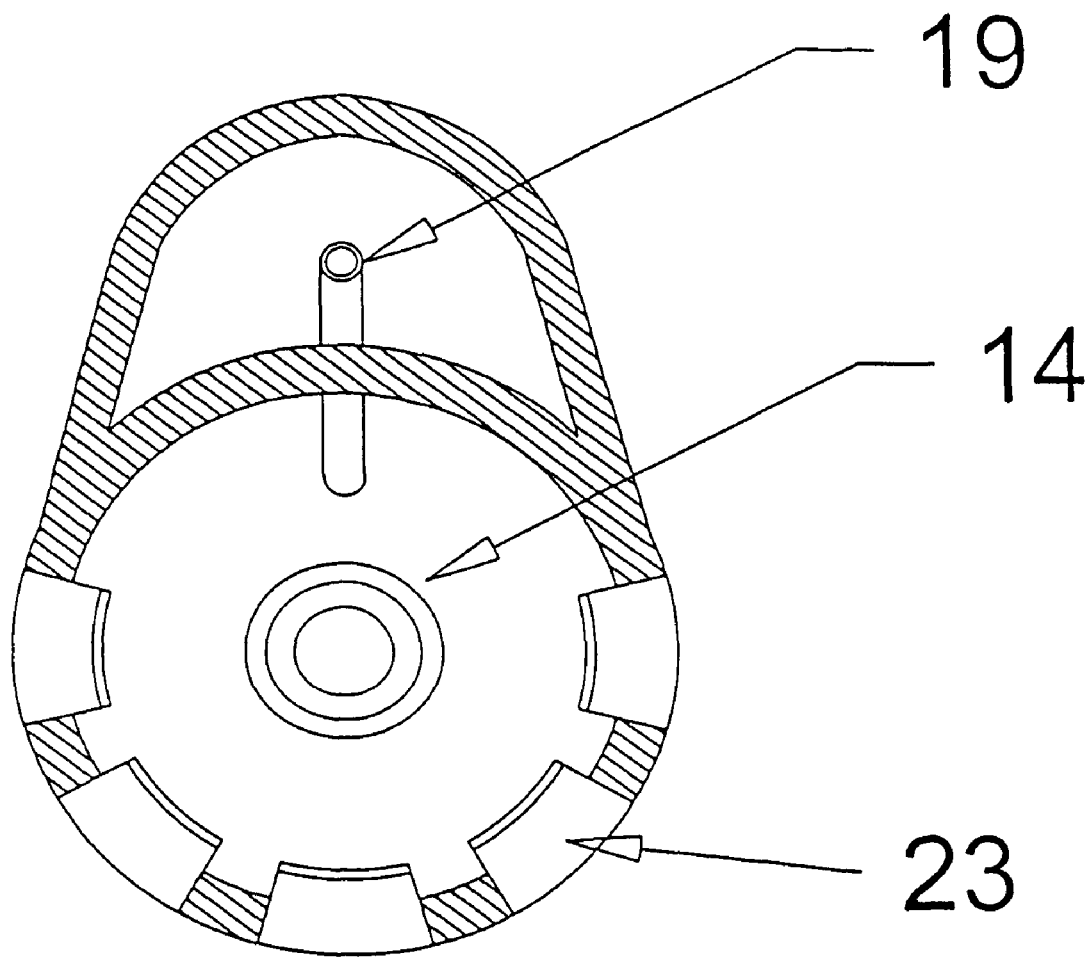

Referring in particular to FIG. 5, a cross sectional view of FIG. 1 section 5-5, shows the spider 43 in cross sectional form. In FIG. 3 the central bearing 44 is held in place by the spider 43 allowing for relatively friction free linear motion of the shaft 8. The spider provides the support for the shuttle cracking pressure spring 9 to place its preloaded force against the shuttle, so that the main contents shutoff valve 13 stays against the main contents valve seat 14 so that it does not leak when not in use. However, the main contents shutoff valve 13 opens when inhalation creates a pressure differential across the shuttle 6 so that subsequent force on the shuttle exceeds the preset spring cracking force. Openings in shuttle 6 permit air initially drawn into the inhalation inlet air vents 23 to pass through the shuttle 6 and into the mouthpiece 4 as illustrated in FIG. 1.

Figure 4:
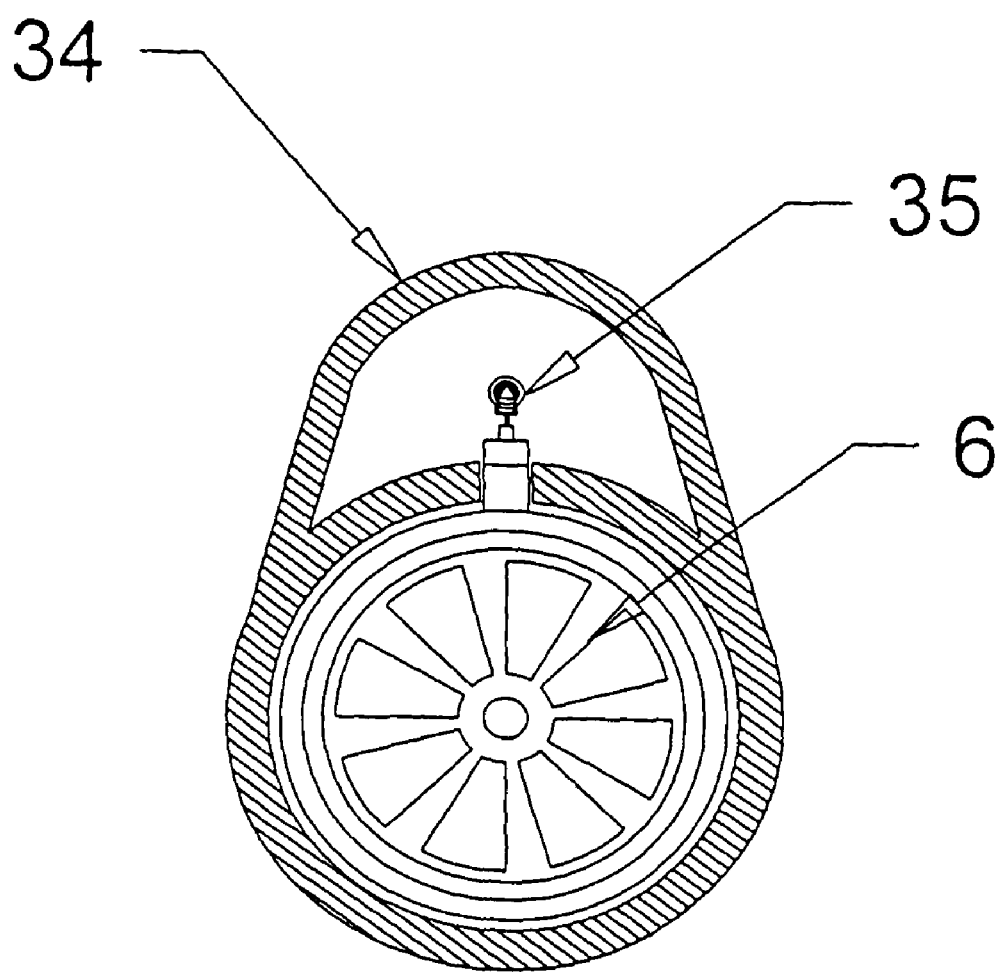
FIG. 4, FIG. 5, and FIG. 6 are cross sections from FIG. 1.
Figure 7:
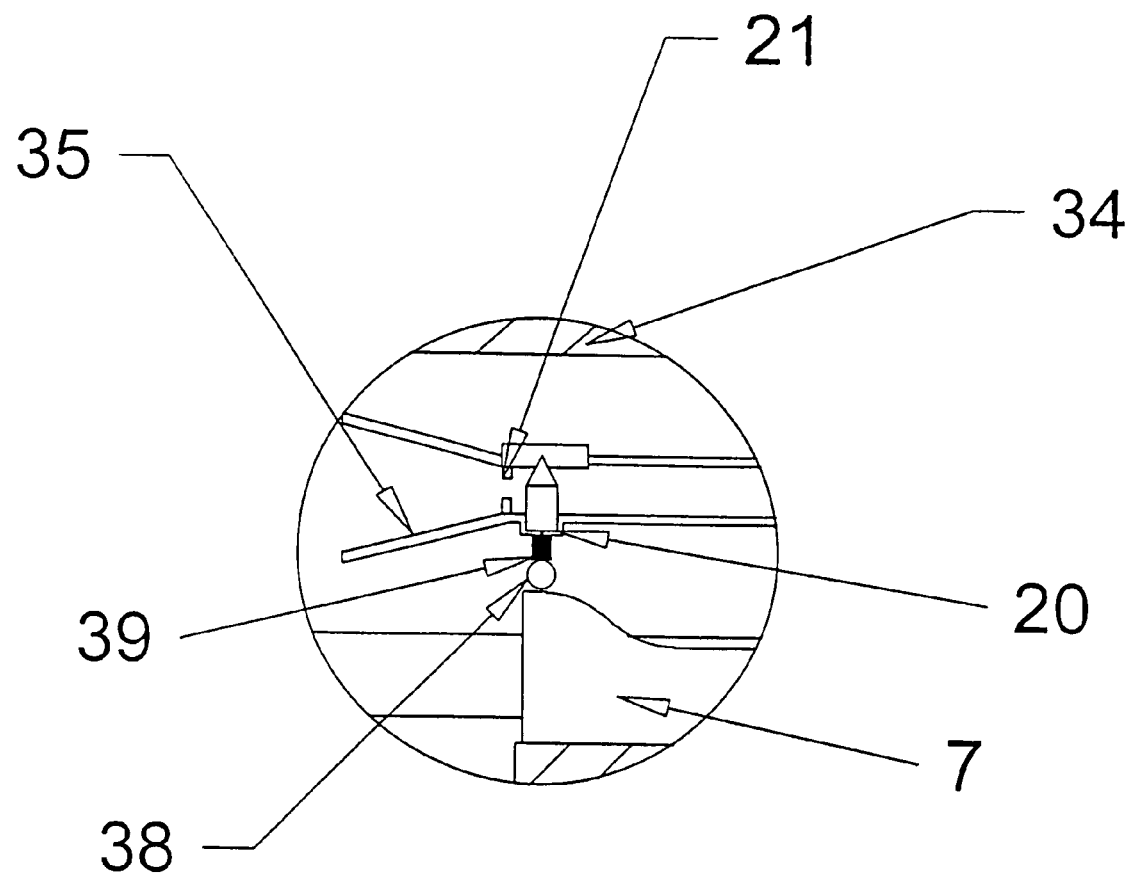
FIG. 7 is a detail of the cam from FIG. 1.

Referring to FIG. 1, FIG. 4 (section 4-4), and FIG. 7, activation of the nasal inhalation system occurs concurrently with the motion of the main shuttle 6, when the attached nasal dispenser shuttle cam 7 allows the opening and shutting of the nasal content valve 20. Valve 20, shown in the shut position, controls flow through the nasal content orifice 21. The nasal dispenser shuttle cam 7, its cam follower 38, and cam follower return spring 39 provide the means to open or shut the nasal content valve 20. The cam 7 profile determines the duration that nasal inhalation solution 29 (shown in FIG. 8) flows. Thus, it can be adjusted for different aroma aerosol solutions.

Referring to 7, as the cam 7 moves during inhalation towards the user's face, the motion of the spring loaded cam follower 38 downwards on the cam 7 determines initiation of flow of nasal solution aerosol spray 29 through the nasal nozzle 35. The nasal aerosol solution is entrained from orifice 21 into the airflow through the nasal entrainment cowling 34 as shown in FIG. 1. When the main shuttle 6 returns to its resting position, the attached cam 7 forces the cam follower 38 upwards and compresses the return spring 39 to allow the nasal content valve 20 to shut, stopping flow of nasal inhalation solution 29.

Referring to FIG. 1 and FIG. 2 the puncture needle protective cover 40 is forced into the needle cover plate detent 42 by the actions of the springs 41, which by virtue of being off center push the lip of the needle protective cover plate over the lip of the detent 42. This prevents the protective cover plate 40 from being pushed inward accidentally and exposing the puncture needles 17 and 18.

Figure 8:
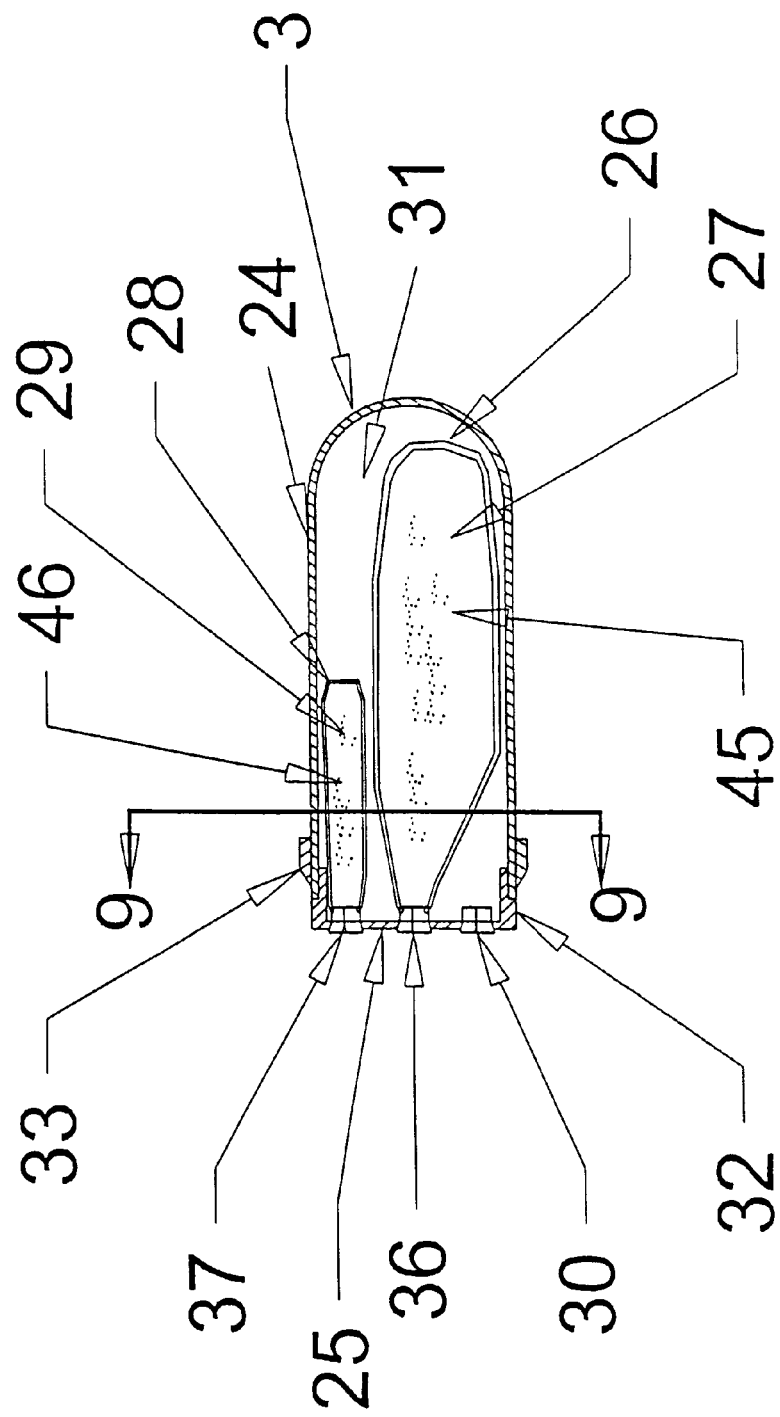
FIG. 8 is a cross sectional side elevation view of a loaded SCADDS cartridge.

Referring to FIG. 8 the bullet shell 24 of the cartridge 3 is connected to the top by a weld 32 that seals the base 25 that supports and is penetrated by the self sealing tops 30 for pressurizing gas 31, 36 for oral inhalation reservoir bag that contains oral inhalation solution 27, and 37 for nasal inhalation reservoir bag 28 containing nasal inhalation solution 29.

Figure 10:
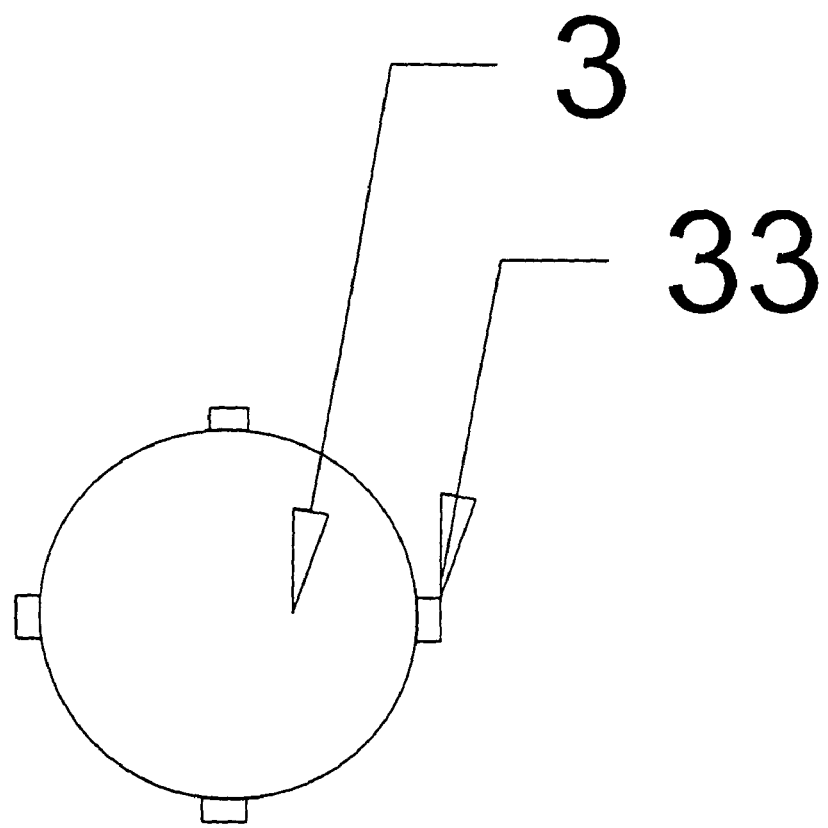
FIG. 10 is a front view of the cartridge in FIG. 8.

FIG. 10 shows a front view of the unattached cartridge 3 with the bayonet snaps 33 that facilitate locking the cartridge 3 into place for activation.

Figure 9:
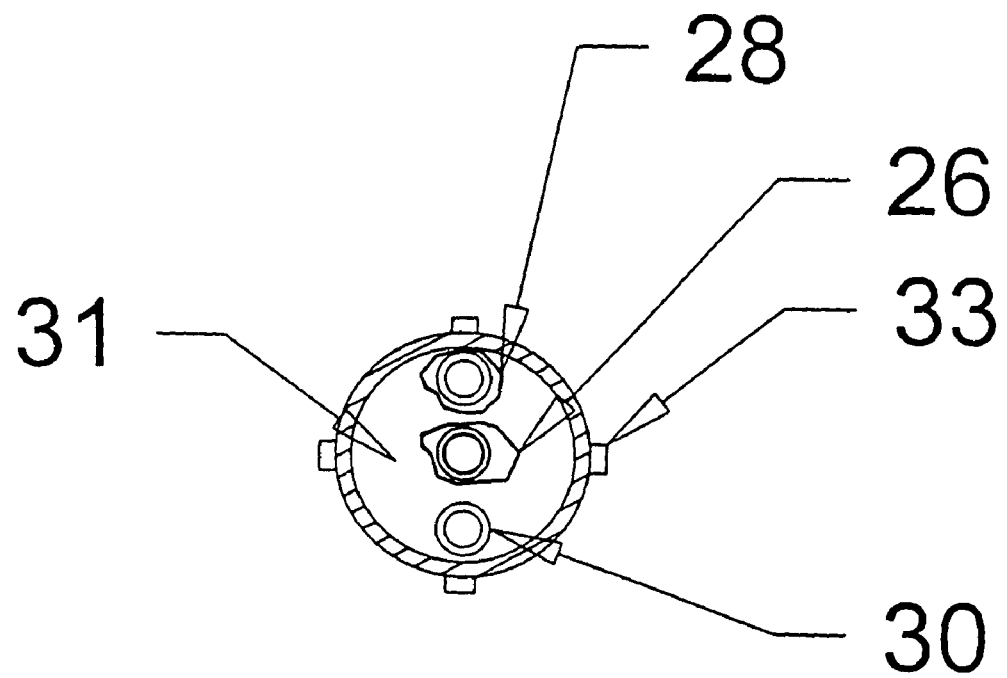
FIG. 9 is a cross sectional view of the cartridge in FIG. 8.

Referring to FIG. 11 when the cartridge assembly 3 is attached to the unit, this action centers the cover plate 40, allowing it to be pushed back by the face of the cartridge assembly bearing the self sealing tops 30, 36, and 37, thus exposing the puncture needles 17 and 18 for use to allow the cartridge 3 to be locked into place as the bayonet snaps 33 (shown in FIG. 8, FIG. 9, and FIG. 10) line up with the cartridge bayonet holders 16 (shown in FIG. 1 without bayonets and FIG. 11 with bayonets held in place.). This action activates the cartridge 3 for subsequent use.

Referring to FIG. 8 and FIG. 11, the mechanism for creating appropriately sized aerosols suitable for inhalation into the most peripheral portions of the respiratory tree is achieved by a combination of the correct pressure, flow rate, orifice size, orifice type, and the dissolved gas 45 and 46 held in solution until the solutions pass through their respective oral and nasal orifices, the main contents valve seat and nozzle 14 and nasal content valve 20, and the dissolved gases 45 and 46 come out of solution and bubbles expand to create large amounts of random kinetic energy further aiding the aerosolization of both oral inhalation solution 27 and nasal inhalation solution 29. These parameters will vary to some extent depending on the solutions being delivered. The cartridge 3 is a self contained bullet shell 24 pressurized vessel with space outside the oral inhalation and nasal inhalation reservoir bags 26 and 28 respectively being pressurized with gas 31 sufficiently to provide driving force against the impermeable solution bags 26 and 28 to contribute to aerosolization. The gas 31 is at sufficient pressure to prevent dissolved gases 45 and 46 from coming out of solution as the bags empty. Self-sealing fill ports 37, 36 and 30 respectively for the nasal inhalation bag 28, the oral inhalation bag 26, and the gas cartridge 3 itself are designed to permit needles to fill the respective containers with the appropriate solution or gas at the same pressure simultaneously. In certain applications the self sealing ports 37, 36, and 30 will be placed in contact with a heat source to melt the top of the ports completely shut to maximize shelf life against evaporation or loss of gas pressure.

Figure 12:
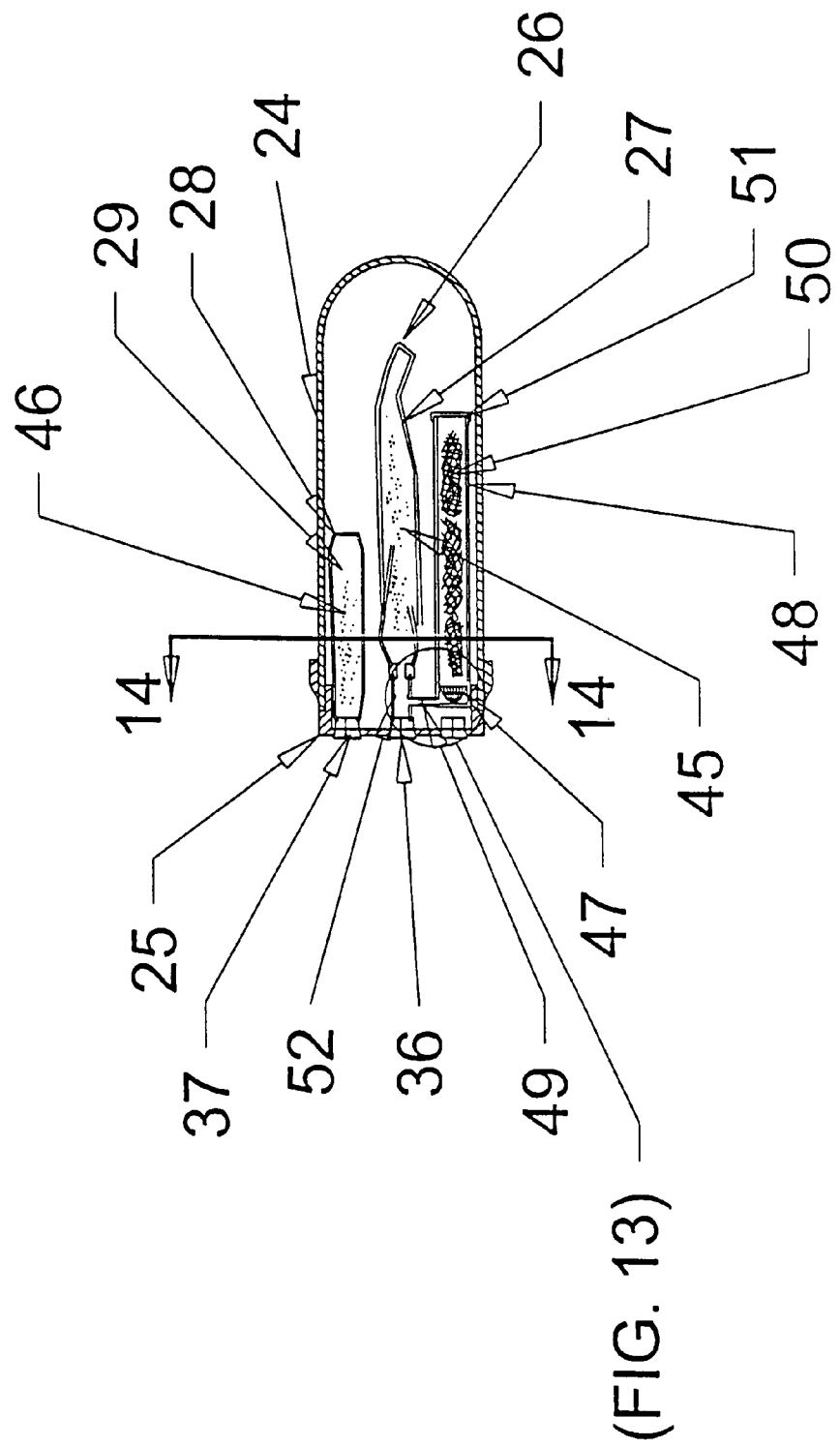
FIG. 12 is a cross sectional side elevation drawing of an embodiment of the Cleantine Cartridge.

Referring to FIG. 12 the recreational tobacco cartridge known as a Cleantine 53 creates appropriately sized aerosols suitable for inhalation into the most peripheral portions of the respiratory tree in the same manner as the SCADDS cartridge 3. This is achieved by a combination of the correct pressure, flow rate, orifice size, orifice type, and the dissolved gas held in solution until the solution passes through the orifice and the dissolved gases 45 and 46 comes out of solution and bubbles expand to create large amounts of random kinetic energy further aiding the aerosolization of both oral inhalation solution 27 and nasal inhalation solution 29. The oral inhalation solution reservoir bag system demonstrates a more complex geometry in the Cleantine shown in FIG. 12 than the oral inhalation bag 26 requires for the SCADDS cartridge 3 shown in FIG. 8.

Figure 13:
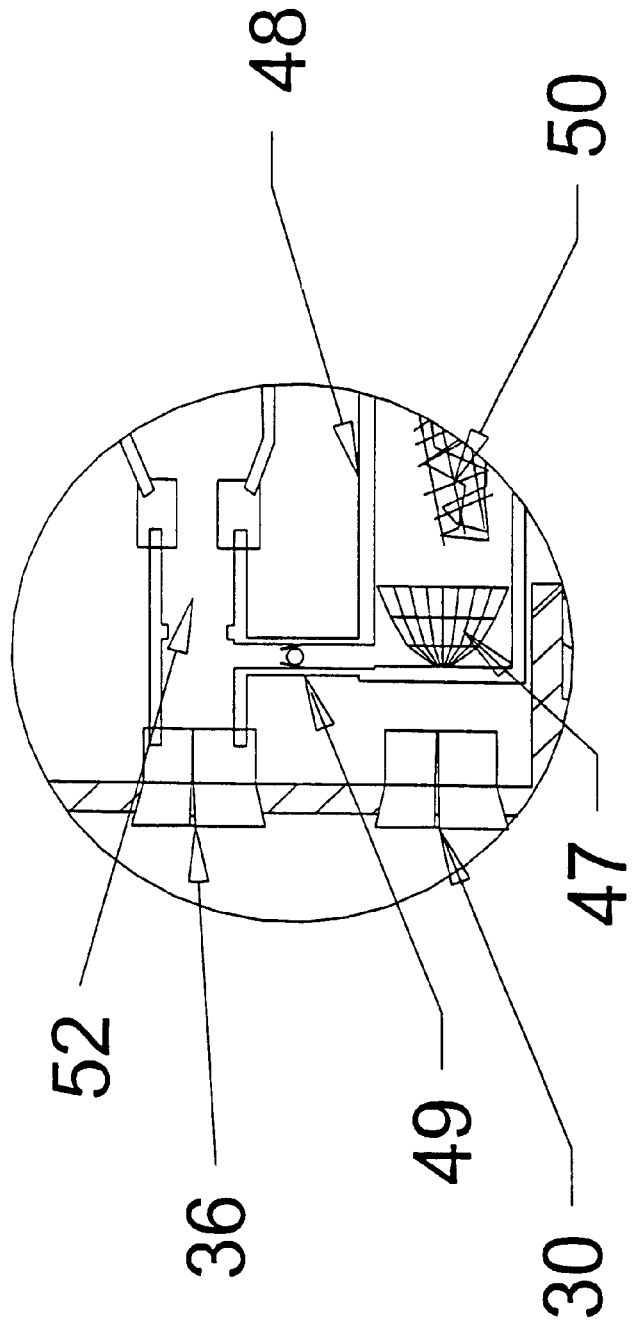
FIG. 13 is a detail view of the one-way valve system initially shown in FIG. 12.

After the fill-port connection 36 in FIG. 12 and FIG. 13 that is a detail of FIG. 12 showing the one-way valve in more detail, a tee connection 49 exists that connects to the portion of the oral inhalation solution bag 26 subject to constant driving pressure. In addition to this portion of the bag the tee connection 49 is connected to an additional reservoir, the tobacco diffusion canister 48 which is capped with a self sealing top 51 that prevents escape of tobacco fragments into interior of the pressurized bullet shell 24 and offers opportunity to load this canister with the tobacco prior to it's insertion into the bullet shell 24. In this secondary reservoir tobacco plant fragments 50 interact with the oral inhalation solution of tobacco extracts dissolved in physiologically buffered saline, or saline, water, or other suitable solution 27 to further enrich the solution's flavor over time. This construction allows the solution to freely circulate between the flexible (oral inhalation reservoir bag 26) and rigid (the tobacco diffusion canister 48) legs of the oral inhalation reservoir bag 26. In order to prevent tobacco fragments from clogging the mechanisms of the unit, a screen or filter 47 to prevent larger particles from escaping and a one-way valve 49 that activates during inhalation are part of the system.

Figure 14:
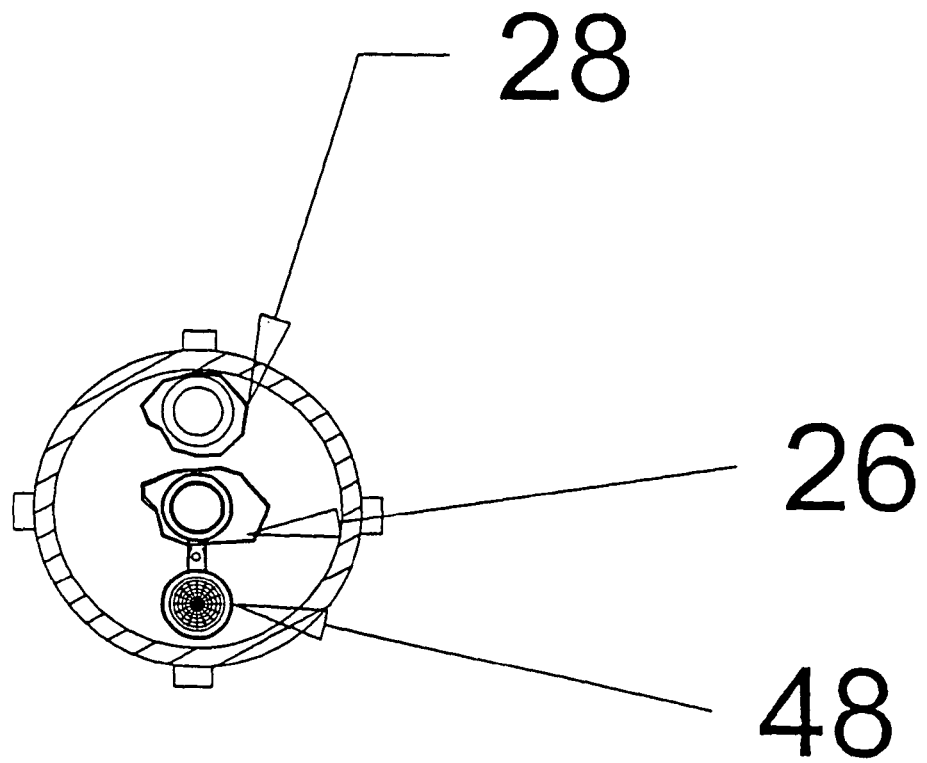
FIG. 14 is a front elevation cross section of the cartridge shown in FIG. 12 through the reservoir bags and tobacco canister.

As illustrated in FIG. 12, FIG. 13, and FIG. 14, which is a cross sectional view of FIG. 12, inside the Cleantine cartridge assembly 53 interior but outside the oral inhalation reservoir bag 26 and nasal inhalation reservoir bag 28, and the tobacco fragments canister 48, is pressurized with gas 31 sufficiently to provide driving force against the impermeable solution bags 26 and 28 to promote aerosolization upon release from main contents valve seat 14. The gas 31 is at sufficient pressure to prevent dissolved gases 45 and 46 from coming out of solution as the bags empty. In the base 25 of the Cleantine cartridge 53 shown in FIG. 12 self-sealing fill ports 37, 36 and 30 respectively for the nasal inhalation bag 28, the oral inhalation bag 26, and the entire Cleantine cartridge 53 are designed to permit needles to simultaneously fill their respective containers with the appropriate solution or gas at the same pressure. In certain applications the self sealing ports 37, 36, and 30 will be placed in contact with a heat source to melt the top of the port to further insure no evaporative loss. Assembly procedure for the Cleantine cartridge assembly 53 is modified to include insertion of tobacco fragments 50 into the tobacco diffusion canister 48 prior to filling the reservoirs with solutions and pressurizing the Cleantine 53 with gas 31.

Figure 15:
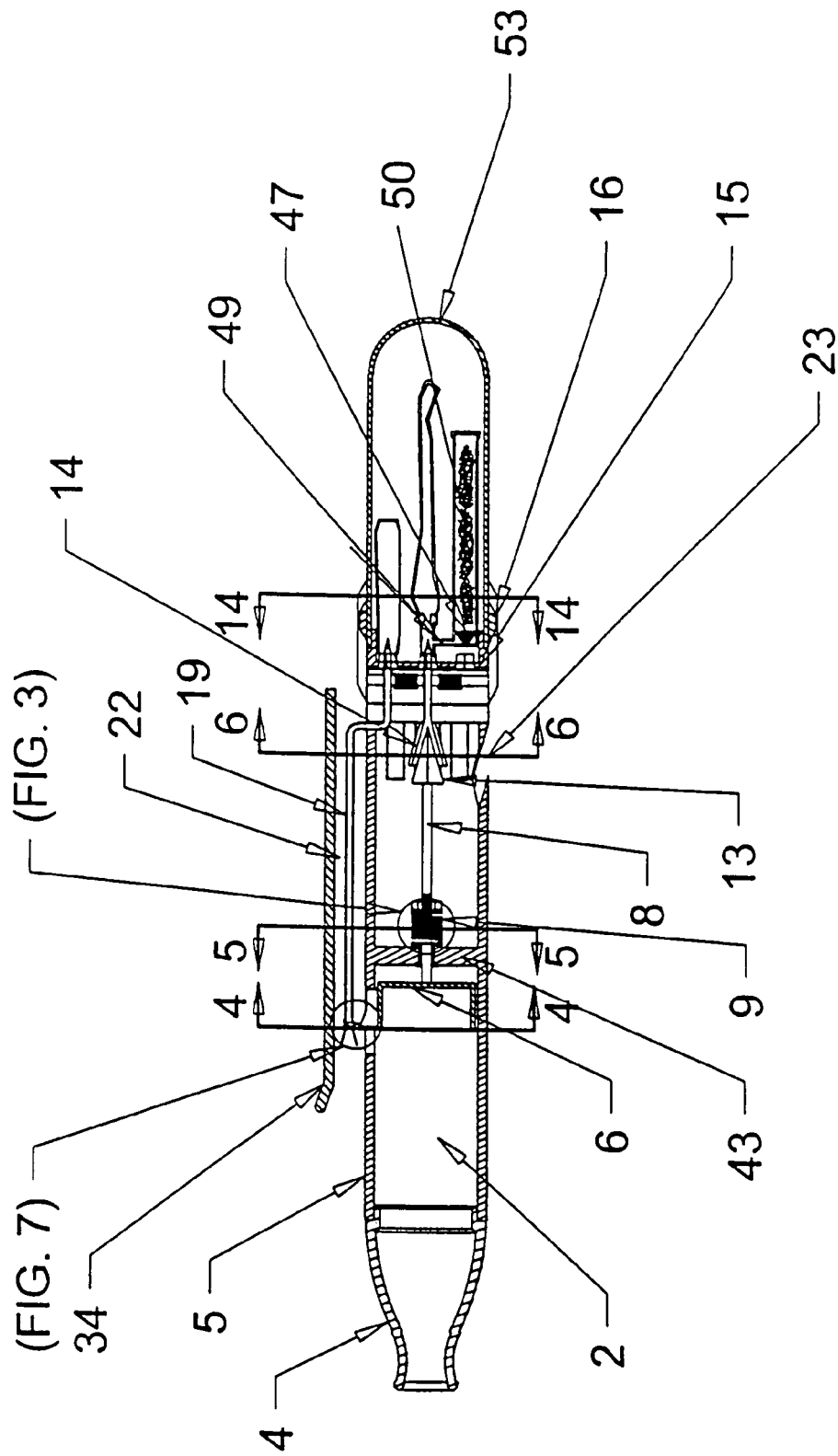
FIG. 15 is a cross sectional side elevation view of a loaded Cigine with a Cleantine cartridge attached illustrating a recreational tobacco embodiment of the SCADDS system.

Referring to FIG. 15 the entire system for recreational tobacco use consist of the previously described Cleantine Cartridge 53 now connected to a basic SCADDS unit 1 with mouthpiece 4 and handle assembly 5 called a Cigine for this application.

Figure 16:
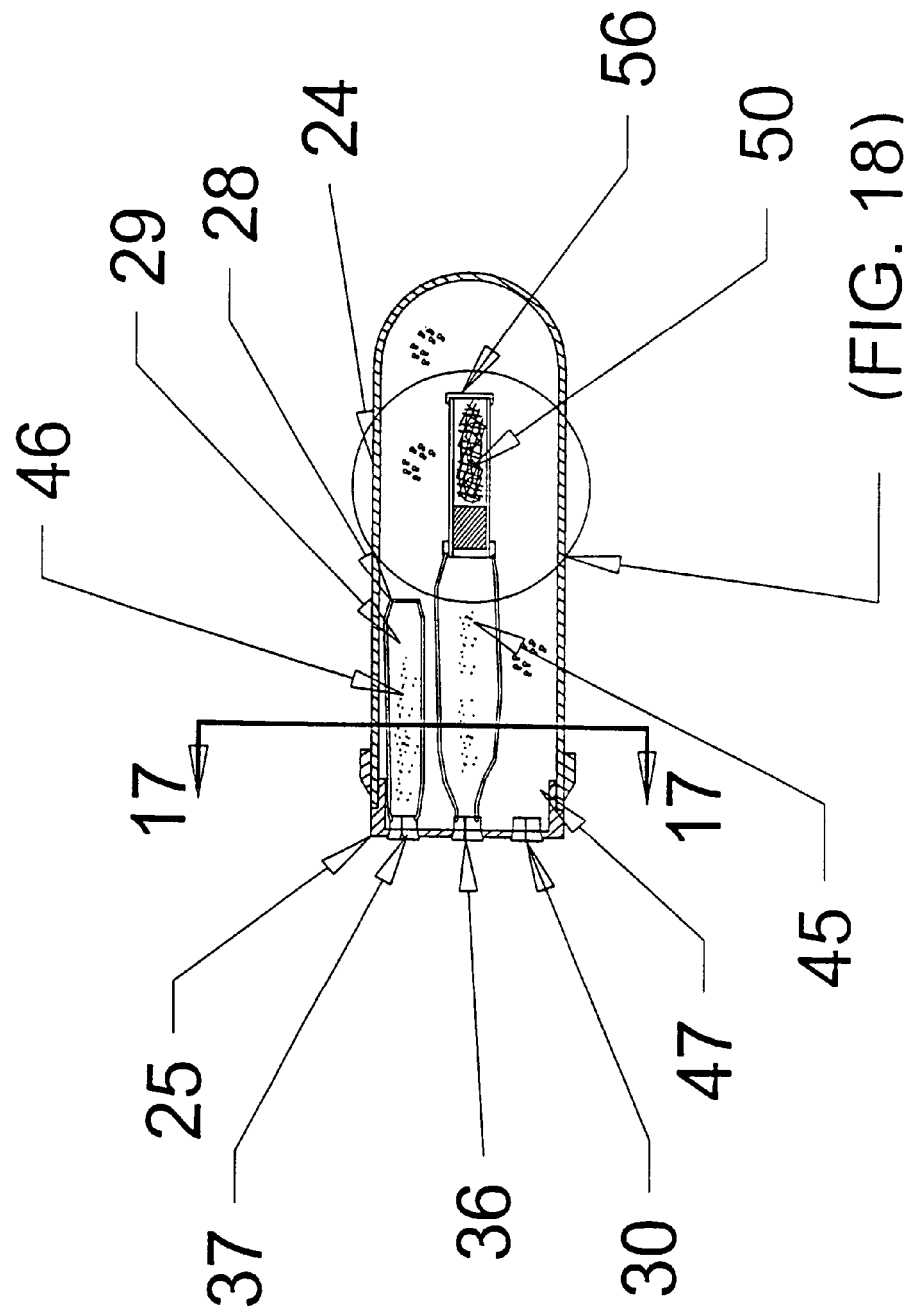
FIG. 16 is a cross sectional side elevation of a Cleantine cartridge embodiment illustrating a filter in use to keep the oral contents valve from being clogged by tobacco fragments.
Figure 17:
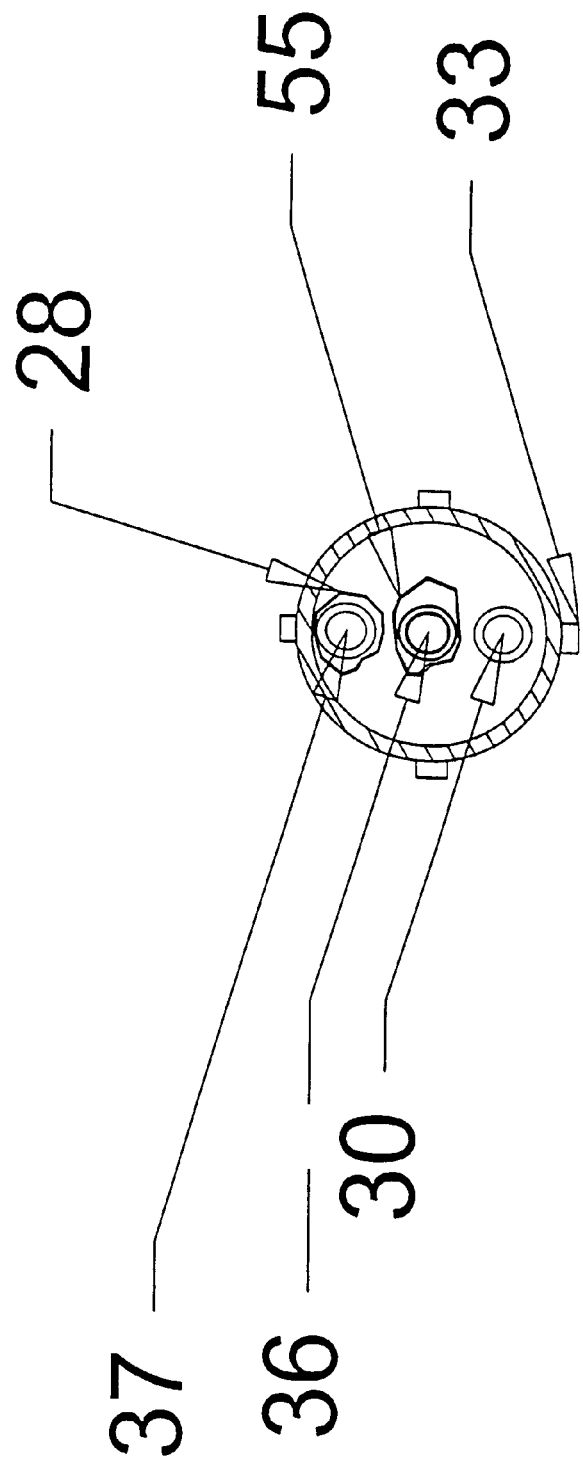
FIG. 17 is a cross sectional front elevation through the reservoir contents bags.
Figure 18:
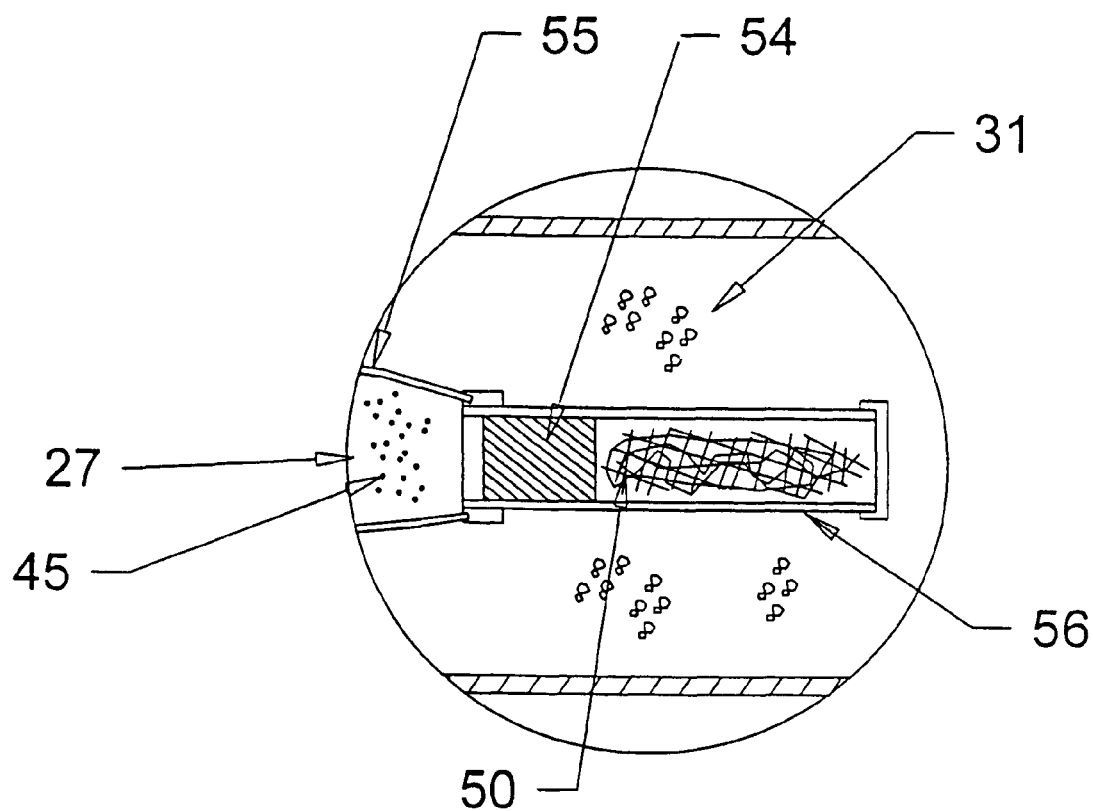
FIG. 18 is a detail view of the flexible tobacco canister and filter junction.

FIG. 16 a side elevation view, FIG. 17 a cross section view from FIG. 16, and FIG. 18 a detail view from FIG. 16 depict an alternate embodiment of the recreational tobacco cartridge known as a Cleantine 53. In this embodiment the flexible fluid contents conduit 55 serves the same function as the oral inhalation reservoir bag 26 with self-sealing top in FIG. 12. A filter 54 is interposed between the flexible oral contents conduit 55 and the semi-rigid tobacco diffusion canister 56. The semi-rigid tobacco diffusion canister 56 serves the same function as the tobacco diffusion canister 48 in FIG. 12, FIG. 13, and FIG. 15. In short, the semi-rigid tobacco diffusion canister supplies a container for tobacco fragments 50 to be bathed in the oral inhalation solution 27 so that more tobacco flavor molecules can continuously enrich the oral inhalation solution 27 as they diffuse back across the filter 54 while tobacco leaf fragments are kept from obstructing the main content puncture needle 17 or the main contents valve seat and nozzle 14. Bayonet snaps 33 to lock this Cleantine 53 into place when activated are shown on an unattached Cleantine cartridge in FIG. 17, the cross section view of FIG. 16 at section 17-17.

After the fill-port connection 36 in FIG. 16 which is detailed in FIG. 18, a filter 54 connects to the flexible oral contents conduit 55 that is subject to driving pressure throughout. In addition to this portion of the bag the filter 54 is connected to an additional reservoir which is the semi-rigid tobacco diffusion canister 56. In this secondary reservoir tobacco plant fragments interact with the solution of tobacco extracts dissolved in physiologically buffered saline, or saline, water, or other suitable solution to further enrich it, improving flavor over time. This construction allows the solution to freely circulate between the flexible conduit 55 and the semi-rigid tobacco canister 56 that serves functionally just like the tobacco diffusion canister 48 described previously in FIG. 12 and FIG. 15. In order to prevent tobacco fragments 50 from clogging the mechanisms of the unit the filter 54 prevents larger particles from escaping into the oral contents flexible conduit 55. Inside the Cleantine cartridge interior but outside the flexible oral contents conduit 55, the semi-rigid tobacco fragments canister 56, and nasal inhalation reservoir bag 28, is pressurized with gas 31 sufficiently to provide driving force against the solutions within the impermeable flexible oral contents conduit 55 and the nasal inhalation reservoir bag 28 to promote aerosolization. The gas 31 is at sufficient pressure to prevent dissolved gases 45 and 46 from coming out of solution as the flexible oral contents conduit 55, semi-rigid tobacco diffusion canister 56, and nasal inhalation reservoir bag empty. In the base 25 of the Cleantine cartridge 53 self-sealing fill ports 36, 37 and 30 respectively for the flexible oral contents conduit 55, the nasal inhalation bag 28, and the entire cartridge 53 itself are designed to permit needles to simultaneously fill the respective containers with the appropriate solution or gas at the same pressure. In certain applications the self sealing ports 36, 37, and the Cleantine cartridge fill port 30 (identical to the SCADDS fill port 30)

will be placed in contact with a heat source to melt the top of the port completely shut to maximize shelf life against evaporation or loss of gas pressure. Assembly procedure for the Cleantine cartridge is modified as mentioned previously in discussion of FIG. 12 to include insertion of tobacco fragments 50 into the semi-rigid tobacco canister 56 prior to filling the flexible oral contents conduit 55 that functions as the oral contents reservoir 26 in this embodiment.

All dose dependent embodiments of the Self Contained Aerosol Dual Delivery System SCADDS utilize sonic orifices such that the flow through the orifice remains constant over designed operating pressures. The cartridge is designed to maintain a driving pressure above the sonic orifice pressure. The gas 31 that pressurizes empty space in the cartridges (Cleantine 53 or cartridge 3) generates this driving pressure.

Figure 19:
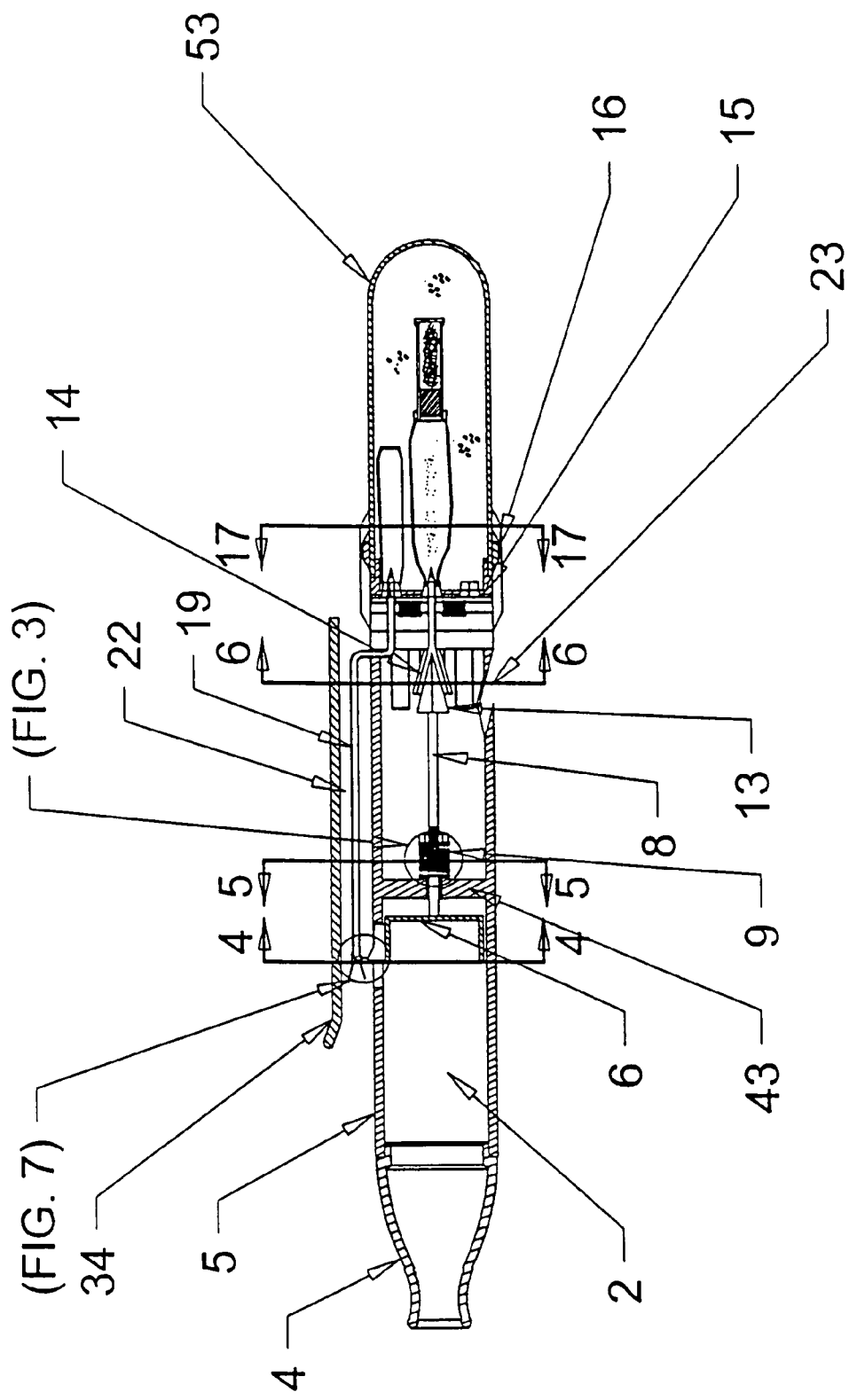
FIG. 19 is a cross sectional side elevation of the Cigine shown in FIG. 15 but now with the alternative Cleantine embodiment illustrating the use of a filter to prevent tobacco fragments from clogging the oral contents orifice valve as illustrated in FIG. 16 but now attached to the Cigine.

Referring to FIG. 19 the entire system for recreational tobacco use in this embodiment consist of the previously described Cleantine Cartridge 53 shown in FIG. 16 now connected to a basic SCADDS unit 1 with mouthpiece 4 and handle assembly 5 again called a Cigine for this application as alternatively illustrated in FIG. 15.

Figure 20:
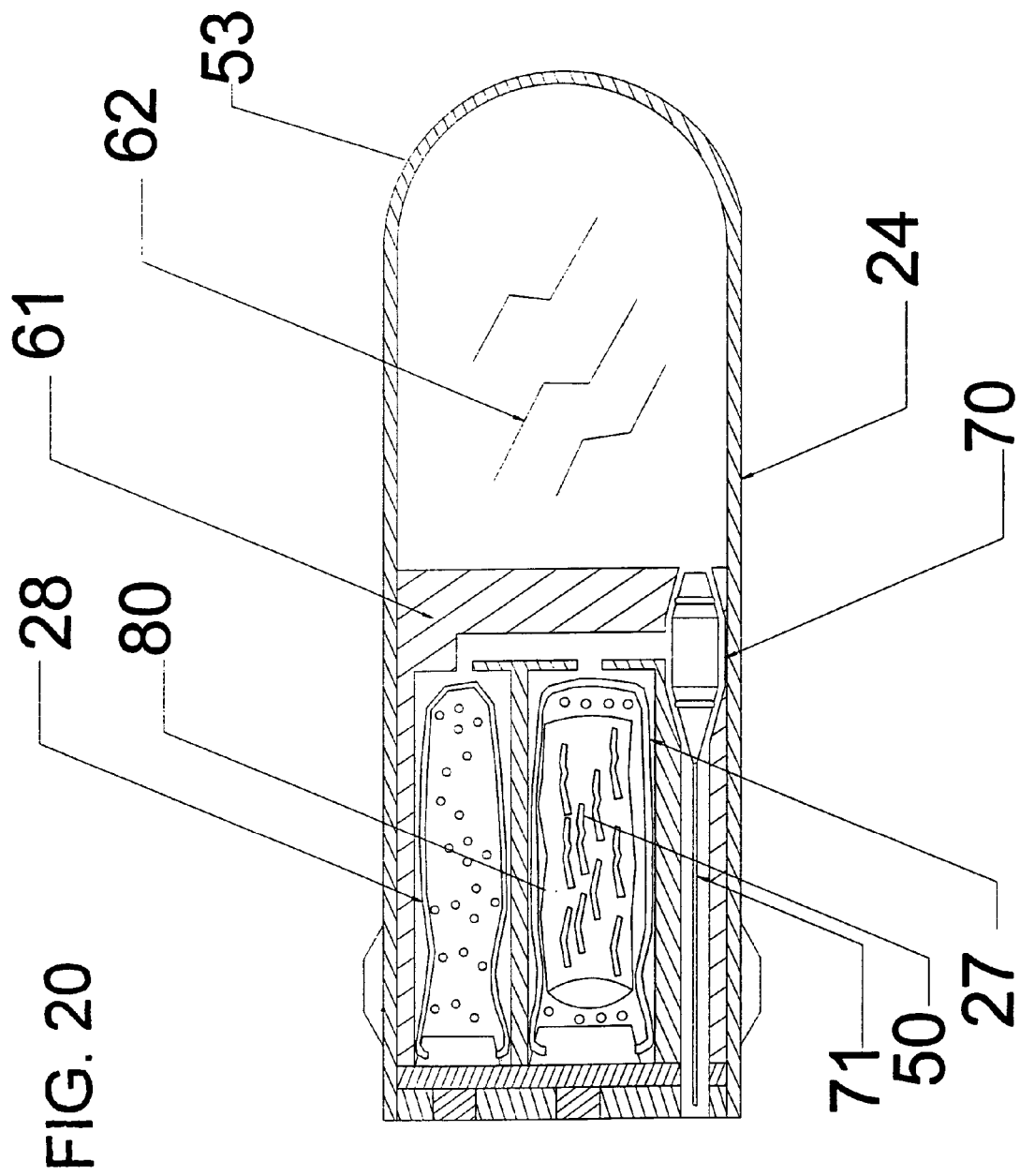
FIG. 20 is a cross sectional side elevation of an alternative Cleantine cartridge.
Figure 21:
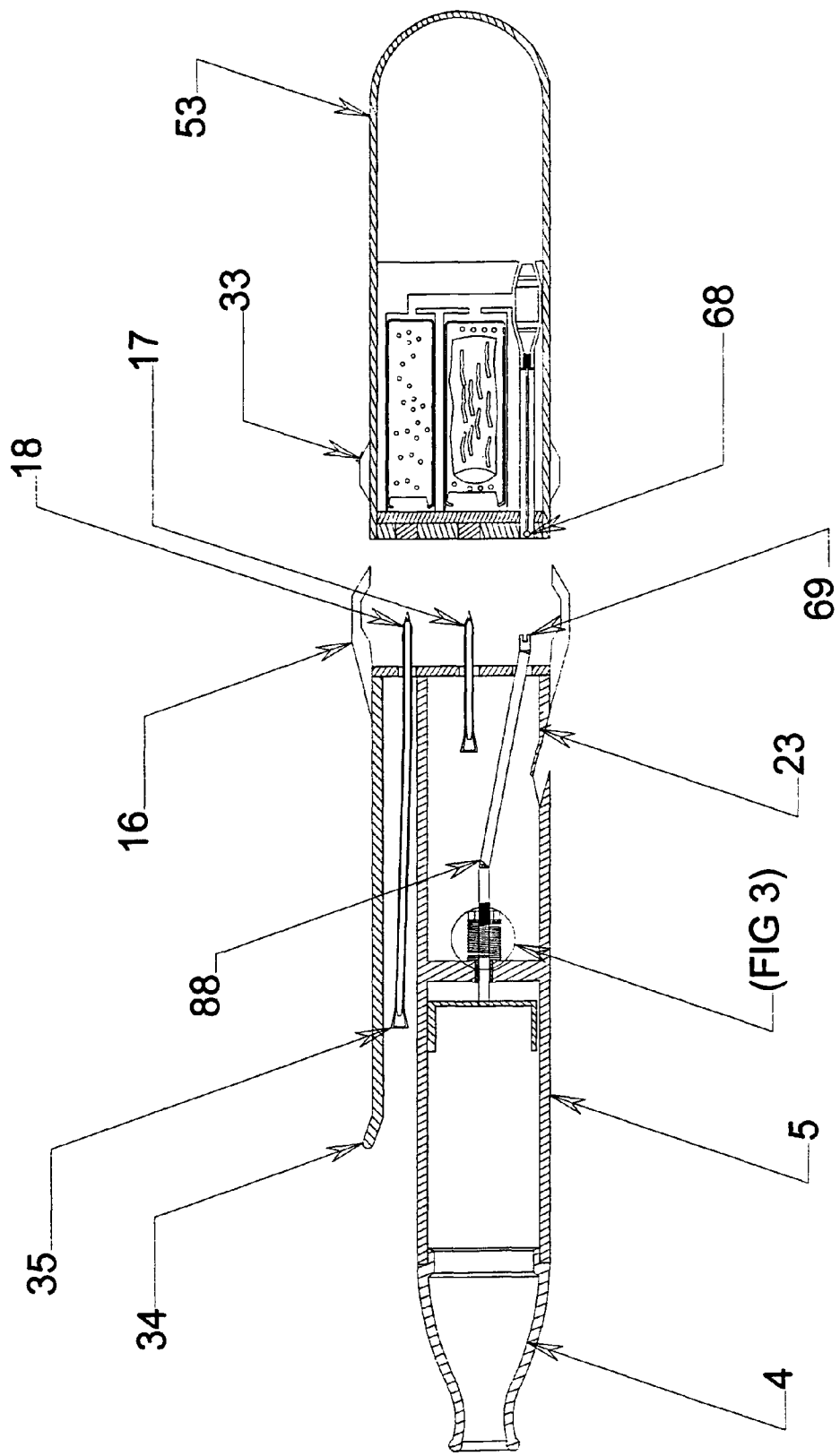
FIG. 21 is a cross sectional side elevation of the Cleantine cartridge of FIG. 20.
Figure 22:
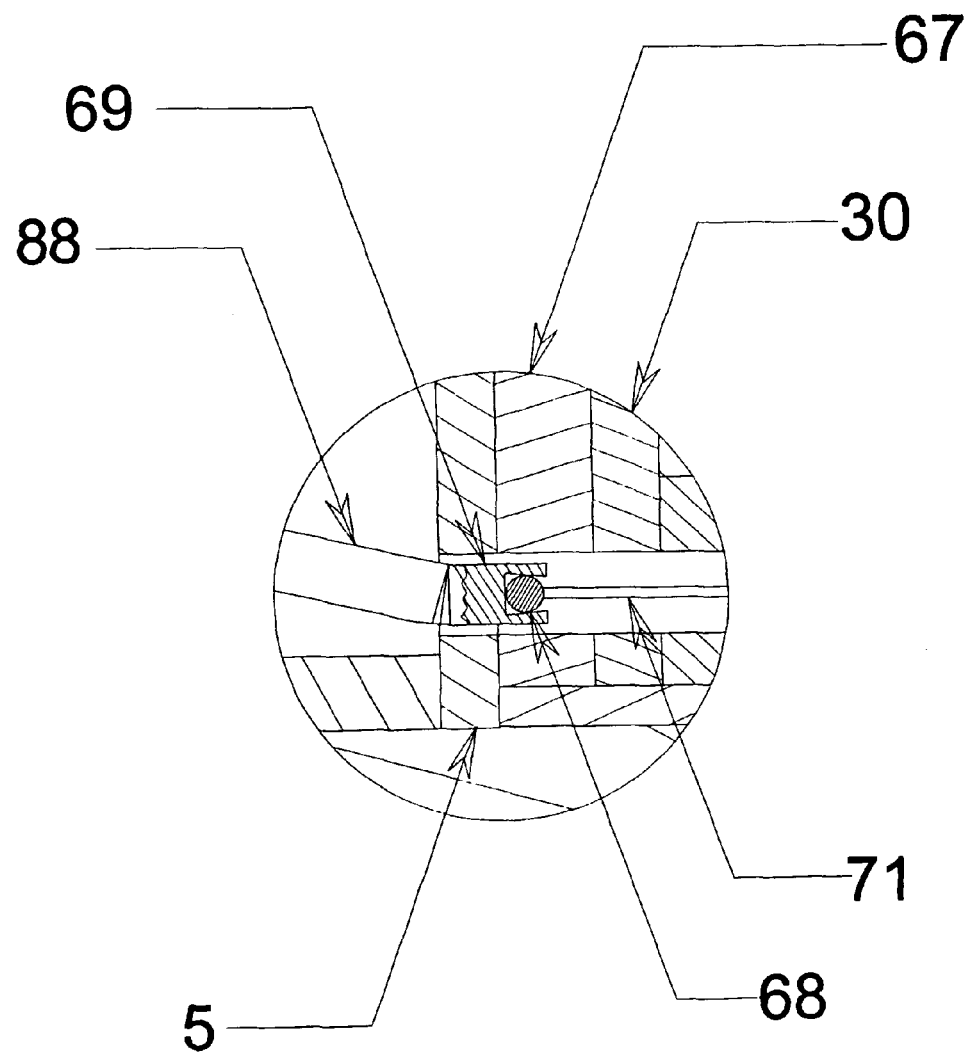
FIG. 22A is a cross sectional side view of the SCADDS Cleantine cartridge of FIG. 20.
FIG. 22B is a cross sectional side view of the SCADDS Cleantine cartridge of FIG. 20 with the shuttle valve.
FIG. 22C is a cross sectional detail of the SCADDS Cleantine cartridge shuttle valve.
Figure 22C:
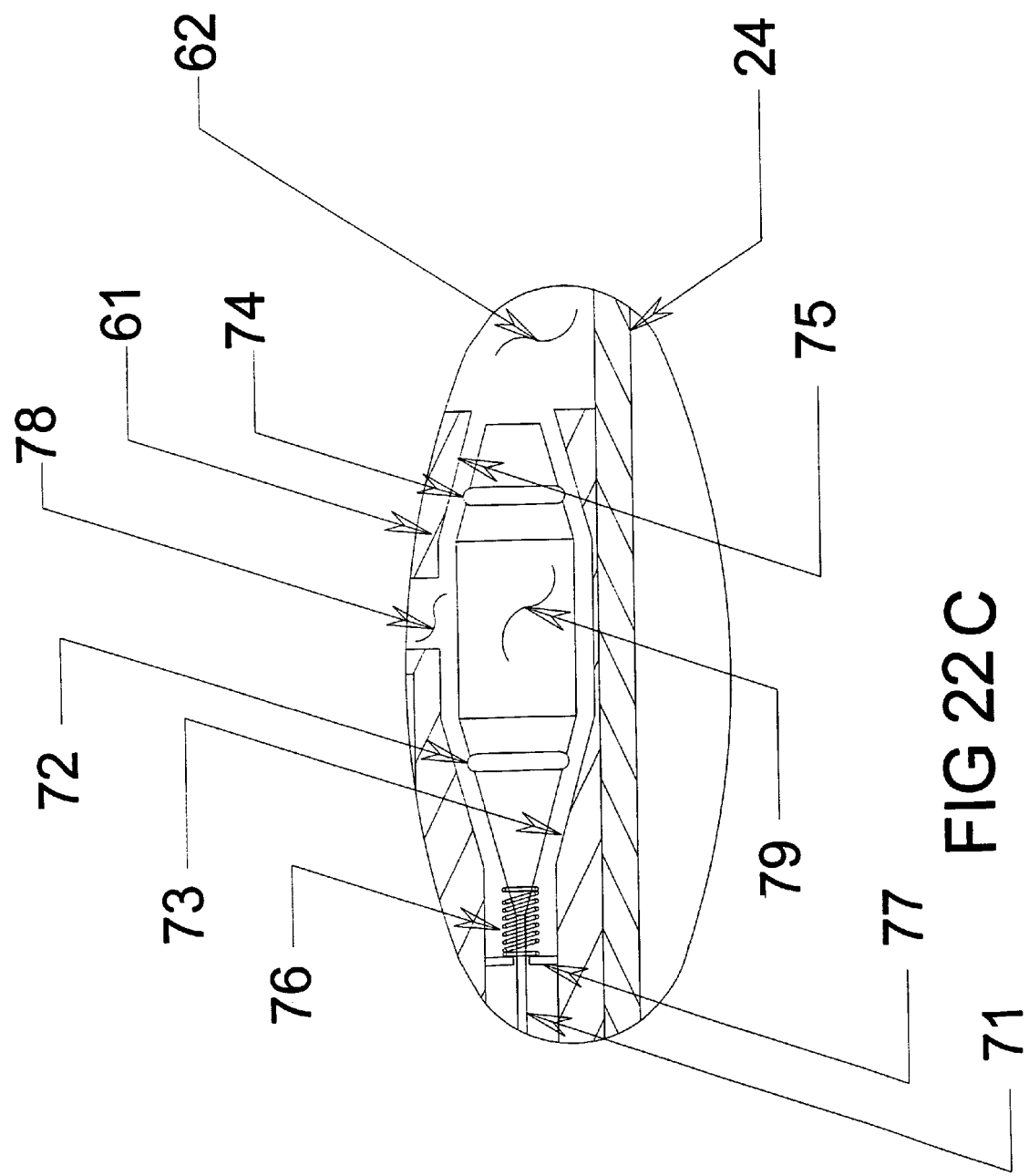

Referring to FIG. 20, FIG. 21, and FIGS. 22A-22C, an alternative embodiment of the Cleantine cartridge 53 is shown in cross sectional view alone in FIG. 20, beside the simplified mouthpiece 4 and central tube 5 or handle assembly 2 known as a Cigine in tobacco applications in FIG. 21, and connected to the mouthpiece handle assembly in FIGS. 22A-22C. FIG. 20 is the cross sectional side elevation of the Cleantine cartridge with a semi-permeable membranous bag containing finely divided solids in the oral inhalation solution and a valve connecting to the pressurized gas reservoir in the cartridge such that when the valve opens the oral and nasal contents bags are under pressure from the gas directed to them via conduits from the gas reservoir. FIG. 21 is a cross sectional side elevation of the Cleantine cartridge of FIG. 20 resting next to the distal end of the SCADDS mouthpiece handle assembly. FIG. 22A is a cross sectional side view of the SCADDS Cleantine cartridge from FIG. 20 now attached to the SCADDS mouthpiece handle assembly such that the penetration needles intrude into the oral inhalation solution bag that contains a semi-permeable membranous bag of finely divided solids that enhance oral inhalation solution properties and into the nasal inhalation solution bag. FIG. 22B shows the shuttle valve flexible connecting shaft attaching to the two way shuttle valve assembly so that when one inhales and the main shuttle in the mouth piece handle assembly moves toward the user in turn the slide valve actuation shuttle will move in the same direction, thus opening the valve to the pressurized gas reservoir, thereby pressurizing the oral and nasal inhalation solution bags to force release of these solutions at sonic orifice speeds leading to their aerosolization and inhalation by the user. FIG. 22C shows the two way shuttle valve assembly in greater detail.

The SCADDS Cleantine cartridge 53 comprises a bulkhead 61 separating the pressurized gas reservoir 62 from the portion of the cartridge containing oral inhalation bag 27 and nasal inhalation bag 28 but still contained within the bullet shell 24 pressure vessel. A semi-membranous bag 80 contains the finely divided tobacco leaf and plant fragments 50 and thus again keeps them from subsequently clogging the penetration needle 17 or nozzle 85.

A two way slide valve assembly 70, consisting of a two way valve with open and closure seals, when opened allows gas to flow through passages to apply pressure to the contents of the aforementioned oral inhalation bag 27 and nasal inhalation bag 28. When the cartridge is connected to the mouthpiece handle assembly 2 the shuttle valve flexible connecting shaft 88 connects with the slide valve actuation shaft 71 via the flexible shaft to cartridge valve connector 69 snapping over the cartridge valve shaft receiving connector 68 (as shown in FIG. 22B) so that motion of the main shuttle 6 in the mouth piece handle assembly opens and shuts the two way slide valve assembly 70 as inhalation pressure increases and then as it decreases the slide valve bias spring 76 shuts the valve.

When the two way shuttle valve assembly 70 is open pressure from the gas reservoir 62 communicates via the spray actuation pressurization passage 78 to deliver pressure to the oral inhalation bag 27 and the nasal inhalation bag 28. When the slide valve main body 79 occludes the actuation pressurization passage 78, in other words when the two-way shuttle valve assembly closes off the actuation pressure passage 78, the remaining driving pressure vents via the slide valve connecting shaft 71 so liquid does not dribble out of the oral nozzle 85 nor the nasal nozzle 35. The flexible shaft 88 functions as in like manner to the shaft 8 in FIG. 1 and others previously described above.

The puncture needle protective cover 40, and needle cover springs 41, and needle cover detent plate 42 shown in FIG. 1 even if not shown in FIG. 21 and FIG. 22A for clarity can certainly be added to this SCADDS device. However, since plastic needles can be used for the penetration needles with appropriate cartridge end plate 67 and cartridge self sealing top 30 materials the necessity to cover the needles for safety purposes is reduced. In the tobacco application users may constantly have the Cleantine Cartridge 53 attached to the Cigine, the basic SCADDS mouthpiece 4 and handle assembly 5 for tobacco dispensing. The distal portion of the handle assembly 5 is shown in FIG. 22B.

Referring to FIG. 21, the alternative Cleantine cartridge 53 of FIG. 20 is shown detached from, but in position to be connected to, the mouthpiece handle assembly 2 via the cartridge bayonet holders 16 which when aligned to snap correctly over the bayonet snaps 33 on the Cleantine cartridge 53 insure proper alignment of the main content puncture needle 17 and nasal content puncture needle 18.

Referring to FIGS. 22A-22C the Cleantine cartridge 53 is now attached to the mouthpiece and handle assembly 2 via the bayonet holders 16 snapping onto the bayonet snaps 33. The main content puncture needle 17 and nasal content puncture needle 18 are shown penetrating the oral inhalation reservoir bag with self sealing top 26 and nasal inhalation reservoir bag with self sealing top 28 respectively such that they now intrude into the oral inhalation solution 27 and nasal inhalation solution 29. Then as the main shuttle is drawn toward the mouthpiece 4, as the user inhales the slide valve assembly connected to the main shuttle via the shuttle valve flexible connecting shaft, then it is drawn into open position releasing pressurized gas from the pressurized compartment beyond the bulkhead to pressurize the reservoir bags 26 and 28 thus forcing fluids to be released as aerosols from the respective oral nozzle 85 and nasal nozzle 35.

While the invention has been described with reference to specific embodiments, modifications and variations of the invention may be constructed without departing from the scope of the invention, which is described in the following claims.

We claim:

1. Self contained aerosol delivery apparatus comprising a handle with first and second ends, a nasal aerosol conduit coupled to the handle, a mouth piece coupled to the first end of the handle, a cartridge connector comprising aerosol coupled to the second end of the handle, air entry openings in the cartridge connector proximal the second end, a movable main shuttle disposed in the cartridge connector, a cartridge comprising first and second compartments, and a valve coupled to the cartridge, the valve being actuatable by the main shuttle when the cartridge is coupled to the handle, wherein the valve is a two way slide valve comprising open and closure seals, and a slide valve actuation shuttle coupled to the seals.

2. The apparatus of claim 1, wherein the cartridge further comprises first and second reservoirs, wherein the valve is mounted in the first compartment of the cartridge, and wherein connecting the handle and the cartridge couples the main shuttle to the actuation shuttle for opening and releasing the aerosol from the second reservoir of the cartridge into the first reservoir and into the second end of the handle for flowing the aerosol into air flowing through the air entry openings, past the main shuttle, through the mouth piece into mouth of a user and through the nasal conduit into nose of the user.

3. The apparatus of claim 2, further comprising a shaft mounted in the handle and having first and second ends, the first end of the shaft being connected to the cartridge connector and the second end of the shaft being connected to the main shuttle, a support for medially supporting the shaft, the support spanning radially inside the handle and having a bearing supporting the shaft for sliding therein.

4. The apparatus of claim 3, further comprising first and second connecting needles mounted in the cartridge connector and extending in an outward direction and a movable wall plate mounted in a receiver comprising first and second openings through which the first and second needles slide in and out of the handle.

5. The apparatus of claim 4, further comprising first and second flexible reservoirs in the first compartment of the cartridge, each reservoir comprising a penetrable seal for respectively connecting the first and second reservoirs to the first and second needles.

6. The apparatus of claim 5, wherein the second compartment of the cartridge comprises pressurized gas retained therein by the valve.

7. The apparatus of claim 6, further comprising fill ports in the cartridge for filling the reservoirs with desired substances, wherein the fill ports are sealable after filling.

8. The apparatus of claim 7, wherein the reservoirs comprise semi-permeable bags comprising desired substances as fine solids, fluids and gases.

9. The apparatus of claim 8, wherein the reservoirs comprise gas and liquid for increasing aerosolization by releasing liquid with dissolved gas coming out of solution transiting through the valve.

10. The apparatus of claim 9, wherein the open and closure seals respectively open and close the second compartment for releasing the pressurized gas responsive to inhalation pressures, and wherein the substances from the bags are expressed as aerosols into the flowing gas for respectively flowing to the mouth and the nose of the users.

11. The apparatus of claim 10, wherein the semi-permeable bags comprise oral inhalation and nasal inhalation bags, wherein contents of each bag are respectively expressed into the nasal conduit for supply to the nose of the user and the mouthpiece for supply to the mouth of the user.

12. The apparatus of claim 11, further comprising a filter connected between the reservoir and the conduit for preventing entry of materials from the semi-permeable bags through the conduit upon flowing of the aerosols.

13. The apparatus of claim 12, further comprising a screen for preventing movement of materials from the bags through the conduit upon flowing of gases out of the reservoirs.

14. The apparatus of claim 2, further comprising a connection between the main shuttle and the actuation shuttle when the cartridge is connected to the handle, and wherein the slide valve open and closure seals respectively open and close responsive to a movement of the main shuttle when inhalation pressure increases and decreases.

15. The apparatus of claim 14, wherein the main shuttle further comprises first and second ends, a nose opening at the first end and an air inlet opening at the second end.

16. A self contained dual aerosol delivery method comprising providing a handle, connecting a replaceable cartridge to the handle, mounting first and second reservoirs in the cartridge, connecting a first conduit to the first reservoir, coupling a mouthpiece to the first conduit, releasing materials from the first reservoir through the first conduit and the mouthpiece into a mouth of a user, connecting a second conduit to the second reservoir, coupling a nasal nozzle to the second conduit, and releasing material from the second reservoir to the second conduit through the nasal nozzle into a nose of a user, further comprising coupling a two way slide valve to the cartridge, moving a main shuttle in the handle, actuating an actuation shuttle in the valve, activating an open and closure seal in the valve upon drawing air into the conduits through the mouthpiece and through the second conduit, and releasing pressurized gas from the cartridge on opening the seal.

17. The method of claim 16, wherein the mounting the reservoirs comprises providing first and second flexible reservoirs, and further comprising filling the first and second flexible reservoirs in the cartridge and filling the cartridge with aerosols for pressurizing the reservoirs in the cartridge.

18. The method of claim 16, further comprising providing semi-permeable bags in the reservoirs, filling the bags with substances of interest, degassing fluids and supplying to the reservoirs for enhancing solubility of organic molecules, dissolving the organic molecules of interest in the degassed fluids exposing the dissolved molecules to gas under pressure in the solutions, aerosolizing the dissolved substances with pressurized gas releases from the cartridge responsive to opening of the two way slide valve.

* * * * *